United States Patent
Chen et al.

(10) Patent No.: US 11,505,815 B2
(45) Date of Patent: Nov. 22, 2022

(54) COMPOSITIONS AND METHODS RELATED TO NON-TEMPLATED ENZYMATIC NUCLEIC ACID SYNTHESIS

(71) Applicant: Nuclera Nucleics Ltd., Cambridge (GB)

(72) Inventors: Michael C. Chen, Cambridge (GB); Gordon R. McInroy, Cambridge (GB)

(73) Assignee: Nuclera Nucleics, Ltd., Cambridge (GB)

(*) Notice: Subject to any disclaimer, the term of this patent is extended or adjusted under 35 U.S.C. 154(b) by 260 days.

(21) Appl. No.: 16/191,109

(22) Filed: Nov. 14, 2018

(65) Prior Publication Data

US 2019/0144905 A1 May 16, 2019

(30) Foreign Application Priority Data

Nov. 14, 2017 (GB) ..................................... 1718804

(51) Int. Cl.
| | |
|---|---|
| C12Q 1/68 | (2018.01) |
| C07H 19/04 | (2006.01) |
| C07H 19/06 | (2006.01) |
| C07H 19/16 | (2006.01) |
| C12P 19/34 | (2006.01) |
| C07H 19/10 | (2006.01) |
| C07H 19/20 | (2006.01) |
| C07H 1/00 | (2006.01) |
| C12Q 1/6844 | (2018.01) |

(52) U.S. Cl.
CPC ................ *C12P 19/34* (2013.01); *C07H 1/00* (2013.01); *C07H 19/04* (2013.01); *C07H 19/06* (2013.01); *C07H 19/10* (2013.01); *C07H 19/16* (2013.01); *C07H 19/20* (2013.01); *C12Q 1/6844* (2013.01)

(58) Field of Classification Search
CPC ....... C12P 19/34; C12Q 1/6844; C07H 19/04; C07H 19/06; C07H 19/10; C07H 19/16; C07H 19/20

See application file for complete search history.

(56) References Cited

U.S. PATENT DOCUMENTS

| | | | |
|---|---|---|---|
| 6,271,212 B1 * | 8/2001 | Chu ....................... | C07H 19/16 514/45 |
| 8,034,923 B1 | 10/2011 | Benner et al. | |
| 2012/0052489 A1 | 3/2012 | Gordon et al. | |
| 2018/0023108 A1 * | 1/2018 | Chen .............. | C12Y 207/07031 435/91.2 |

FOREIGN PATENT DOCUMENTS

| | | |
|---|---|---|
| IT | FI20070077 A1 | 9/2008 |
| WO | WO 86/06253 | 11/1986 |
| WO | WO 2016/128731 A1 | 8/2016 |
| WO | WO-2016128731 A1 * | 8/2016 ............. C12P 19/34 |
| WO | WO 2017/087887 A1 | 5/2017 |

OTHER PUBLICATIONS

Daniel Hutter et al: "Labeled Nucleoside Triphosphates with Reversibly Terminating Aminoalkoxyl Groups", 2010. Nucleosides, Nucleotides & Nucleic Acids, vol. 29 (11-12), pp. 879-895 (Year: 2010).*

Fàbrega, C., Güimil García, R., Díaz, A.R., Eritja, R. Studies on the synthesis of oligonucleotides containing photoreactive nucleosides: 2-azido-2'-deoxyinosine and 8-azido-2'-deoxyadenosine. 1998, Biol. Chem., 379(4-5), 527-533 (Year: 1998).*

Agarwal, et al., "Deoxyoligonucleotide synthesis using a new phosphate protecting group," J. Am. Chem. Soc., vol. 95, No. 6, pp. 2020-2021, Mar. 1, 1973.

Agarwal, et al., "Total Synthesis of the Structural Gene for the Precursor of a Tyrosine Suppressor Transfer RNA from *Escherichia coli*," Journal of Biological Chemistry, vol. 251, No. 3, pp. 624-633, Feb. 10, 1976.

Cartwright, et al., "Azidopolynucleotides as photoaffinity reagents," Nucleic Acids Research, vol. 8, No. 7, pp. 1675-1691, 1980.

Chen, et al., "Reconstructed evolutionary adaptive paths give polymerases accepting reversible terminators for sequencing and SNP detection," Proceedings of the National Academy of Sciences of the United States of America, vol. 107, No. 5, pp. 1948-1953, Jan. 11, 2010.

Hammond, et al., "The L protein of vesicular stomatitis virus transcription complexes is specifically photolabelled by 5-azidouridine 5'-triphosphate, an analogue of the RNA polymerase substrate uridine 5'-triphosphate," J. of General Virology, vol. 73, No. 1, pp. 61-66, 1992.

Hutter, et al., "Labeled Nucleoside Triphosphates with Reversibly Terminating Aminoalkoxyl Groups," Nucleosides, Nucleotides and Nucleic Acids, vol. 29, No. 11-12, pp. 879-895, Nov. 30, 2010.

Jerome, et al., "Preparation of A Fluorescent GTP Analogue: Tetrazolo-oxo-purine nucleoside triphosphate," J. of Biochemical and Biophysical Methods, vol. 3, No. 3, pp. 187-190, 1980.

Knoll, et al., "Mapping of the active site of T7 RNA polymerase with 8-azidoATP," Biochimica et Biophysica Acta, vol. 1121, No. 3, pp. 252-260, 1992.

Kuboki, et al., "Synthesis of Regioselectively Protected Forms of Cytidine Based on Enzyme-catalyzed Deacetylation as the Key Step," Bicosco. Biotech. Biochem., vol. 64, No. 2, pp. 363-368, Jan. 1, 2000.

Meher, et al., "Nucleobase Protection of Deoxyribo-and Ribonucleosides," Current Protocols in Nucleic Acid Chemistry, pp. 2.1.1-2.1.40, Jun. 19, 2017.

Owens, et al., "Characterization of the Guanosine-3'-diphosphate-5'-diphosphate Binding Site on *E. coli* RNA Polymerase Using a Photoprobe, 8-Az idoguanos ine- 3'-5'-B isphosphate," Biochemical and Biophysical Research Comms., vol. 142, No. 3, pp. 964-971, 1987.

(Continued)

*Primary Examiner* — Jezia Riley
(74) *Attorney, Agent, or Firm* — Morgan, Lewis & Bockius, LLP

(57) ABSTRACT

The invention relates to the use of an amine masked moiety in a method of enzymatic nucleic acid synthesis. The invention also relates to said amine masked moieties per se and a process for preparing nucleotide triphosphates comprising said amine masked moieties.

6 Claims, 21 Drawing Sheets

(56) References Cited

OTHER PUBLICATIONS

Quiggle, et al., "Design of New Photaffinity Labels for Ribosomal Peptidyltransferase," Biochemistry, vol. 17, No. 1, pp. 94-101, 1978.
Ramsinghani, et al., "Syntheses of Photoactive Analogues of Adenosine Diphosphate (Hydroxymethyl)pyrrolidinediol and Photoaffinity Labeling of Poly(ADP-ribose) Glycohydrolase," Biochemistry, vol. 37, No. 21, pp. 7801-7812, May 1, 1998.
Rush, et al., "Photoaffinity Labeling of the Klenow Fragment with 8-Azido-dATP," J. of Biological Chem., vol. 265, No. 9, pp. 4821-4827, 1990.
Taniguchi, et al., "Discrimination Between 8-Oxo-2'-Deoxyguanosine and 2'-Deoxyguanosine in DNA by the Single Nucleotide Primer Extension Reaction with Adap Triphosphate," Angewandte Chemie International Edition, vol. 54, No. 17, pp. 5147-5151, Apr. 20, 2015.

\* cited by examiner

COMPOSITIONS AND METHODS RELATED TO NON-TEMPLATED ENZYMATIC NUCLEIC ACID SYNTHESIS

FIELD OF THE INVENTION

The invention relates to the use of an amine masked moiety in a method of enzymatic nucleic acid synthesis. The invention also relates to said amine masked moieties per se and a process for preparing nucleotide triphosphates comprising said amine masked moieties.

BACKGROUND OF THE INVENTION

Nucleic acid synthesis is vital to modern biotechnology. The rapid pace of development in the biotechnology arena has been made possible by the scientific community's ability to artificially synthesise DNA, RNA and proteins.

Artificial DNA synthesis—a £1 billion and growing market—allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. While the benefits of DNA synthesis are numerous, an oft-mentioned problem prevents the further growth of the artificial DNA synthesis industry, and thus the biotechnology field. Despite being a mature technology, it is practically impossible to synthesise a DNA strand greater than 200 nucleotides in length, and most DNA synthesis companies only offer up to 120 nucleotides. In comparison, an average protein-coding gene is of the order of 2000-3000 nucleotides, and an average eukaryotic genome numbers in the billions of nucleotides. Thus, all major gene synthesis companies today rely on variations of a 'synthesise and stitch' technique, where overlapping 40-60-mer fragments are synthesised and stitched together by PCR (see Young, L. et al. (2004) *Nucleic Acid Res.* 32, e59). Current methods offered by the gene synthesis industry generally allow up to 3 kb in length for routine production.

The reason DNA cannot be synthesised beyond 120-200 nucleotides at a time is due to the current methodology for generating DNA, which uses synthetic chemistry (i.e., phosphoramidite technology) to couple a nucleotide one at a time to make DNA. As the efficiency of each nucleotide-coupling step is 95.0-99.0% efficient, it is mathematically impossible to synthesise DNA longer than 200 nucleotides in acceptable yields. The Venter Institute illustrated this laborious process by spending 4 years and 20 million USD to synthesise the relatively small genome of a bacterium (see Gibson, D. G. et al. (2010) *Science* 329, 52-56).

Known methods of DNA sequencing use template-dependent DNA polymerases to add 3'-reversibly terminated nucleotides to a growing double-stranded substrate (see, Bentley, D. R. et al. (2008) *Nature* 456, 53-59). In the 'sequencing-by-synthesis' process, each added nucleotide contains a dye, allowing the user to identify the exact sequence of the template strand. Albeit on double-stranded DNA, this technology is able to produce strands of between 500-1000 bps long. However, this technology is not suitable for de novo nucleic acid synthesis because of the requirement for an existing nucleic acid strand to act as a template.

The —ONH$_2$ chemical moiety is useful in a variety of biotechnology applications, such as sequencing-by-synthesis (SBS), templated enzymatic DNA synthesis, and non-templated enzymatic DNA synthesis (D. Hutter et al., Nucleosides Nucleotides Nucleic Acids. 29 (2010) 879-895.). Specifically, the utility of the —ONH$_2$ chemical moiety rests in its ability to reversibly mask the —OH functional group, for example the 3'-OH position on 2'-deoxyribose or ribose in nucleotide 5'-triphosphates. Additionally, the small size of the —ONH$_2$ chemical moiety makes it a better substrate for enzymes such as polymerases, as opposed to other reversibly terminating moieties such as —OCH$_2$N$_3$. However, the conditions required for the deprotection of the —ONH$_2$ chemical moiety are disadvantageous. A common chemical used to convert —ONH$_2$ to —OH is sodium nitrite under acidic conditions. Problematically, oxidative deamination of adenine, guanine and cytosine occur at an appreciable rate in the presence of sodium nitrite, as shown in FIGS. 1 and 4 as well as numerous previous studies (F. Kaudewitz, Nature. 183 (1959) 1829-1830, F. Kodama et al., Mutat. Res. 40 (1976) 119-124, R. Shapiro and S. H. Pohl, Biochemistry. 7 (1968) 448-455). Deamination of these bases converts adenine to hypoxanthine, cytosine to uracil and guanine to xanthine. These conversions result in appreciable mutations, as hypoxanthine pairs with cytosine and uracil pairs with adenine. Such mutations thus limit the practical utility of the —ONH$_2$ reversible terminator, particularly in non-templated enzymatic DNA synthesis for synthetic biology applications.

The addition of flavonoids and other phenolic compounds has been proposed as a potential solution to reduce nucleic acid nitrogenous heterocycle deamination in the presence of sodium nitrite (C. Oldreive et al., Chem. Res. Toxicol. 11 (1998) 1574-1579). Whilst previous studies have shown that certain additives prevent nucleic acid base deamination, the same additives will also inhibit the conversion of 3'-ONH$_2$ to 3'-OH required to effect reversible termination.

Thus, the use of flavonoids and other phenolic compounds are of limited utility to non-templated enzymatic DNA synthesis.

There is therefore a need to provide an improved method of nucleic acid synthesis that is able to overcome the problems associated with currently available methods.

SUMMARY OF THE INVENTION

According to a first aspect of the invention, there is provided the use of an amine masked derivative of a nitrogenous heterocycle, such as adenine, guanine, cytosine, isoguanine, isocytosine and 2,6-diaminopurine in a method of enzymatic nucleic acid synthesis.

According to a further aspect of the invention, there is provided the use of a compound of formula (I):

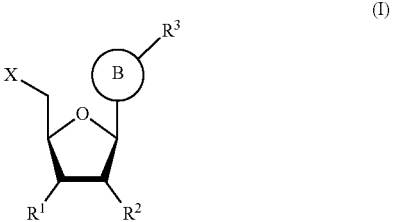

wherein:

R¹ represents a moiety capable of being unmasked to reveal a hydroxyl group, including —H, —OH, —ONH₂, —ONC(CH₃)₂, —OCH₂N₃, —OCH₂CHCH₂, —OPO₂²⁻, —OCH₂SSCH₂CH₃, —OCOCH₃, —OCH₂CH₂CN, —O-methoxyethyl, —O-alkyl, or —O-alkoxy;

R² represents —H, —OH, —ONH₂, —ONC(CH₃)₂, —OCH₂N₃, —OCH₂CHCH₂, —OPO₃²⁻, —OCH₂SSCH₂CH₃, —OCOCH₃, —OCH₂CH₂CN, —O-methoxyethyl, —O-alkyl, or —O-alkoxy or any other molecular moiety;

X represents an —OH group or one or more phosphate, phosphorothioate, boranophosphate or imidophosphate groups, or any combination thereof, wherein said group is capable of endowing competence for enzymatic addition;

R³ represents an amine masking group, wherein said amino group would be involved in hydrogen bond base-pairing with a complementary base and deamination of said amino group could result in altered hydrogen bonding with a complementary base; and B represents a nitrogenous heterocycle;

in a method of enzymatic nucleic acid synthesis.

According to a further aspect of the invention, there is provided a compound of formula (I)ᵃ:

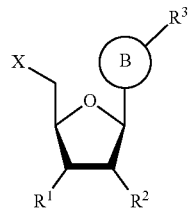

(I)ᵃ wherein:

R¹ represents a moiety capable of being unmasked to reveal a hydroxyl group, including —H, —OH, —ONH₂, —ONC(CH₃)₂, —OCH₂N₃, —OCH₂CHCH₂, —OPO₃²⁻, —OCH₂SSCH₂CH₃, —OCOCH₃, —OCH₂CH₂CN, —O-methoxyethyl, —O-alkyl, or —O-alkoxy;

R² represents —H, —OH, —ONH₂, —ONC(CH₃)₂, —OCH₂N₃, —OCH₂CHCH₂, —OPO₃²⁻, —OCH₂SSCH₂CH₃, —OCOCH₃, —OCH₂CH₂CN, —O-methoxyethyl, —O-alkyl, or —O-alkoxy or any other molecular moiety;

X represents one or more phosphate, phosphorothioate, boranophosphate or imidophosphate groups, or any combination thereof, wherein said group is capable of endowing competence for enzymatic addition;

R³ represents an amine masking group, wherein said amino group would be involved in hydrogen bond base-pairing with a complementary base and deamination of said amino group could result in altered hydrogen bonding with a complementary base; and B represents a nitrogenous heterocycle.

According to a further aspect of the invention, there is provided a process of preparing a compound of formula (V):

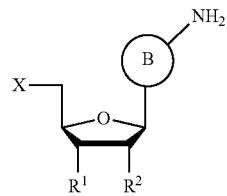

(V)

wherein X, R¹, R² and B are as defined herein, which comprises reacting a compound of formula (I):

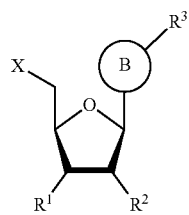

(I)

wherein X, R¹, R², R³ and B are as defined herein, with a chemical, with electromagnetic radiation, with heat and/or with an electric current.

According to a further aspect of the invention, there is provided a process of preparing a compound of formula (II), (III) or (IV):

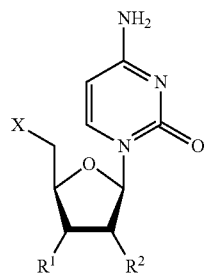

(II)

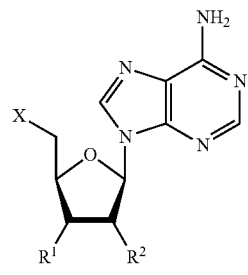

(III)

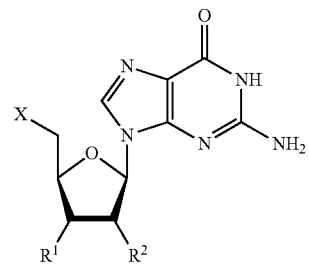

(IV)

wherein X, $R^1$ and $R^2$ are as defined herein, which comprises reacting a compound of formula $(II)^a$, $(III)^a$ or $(IV)^a$, respectively:

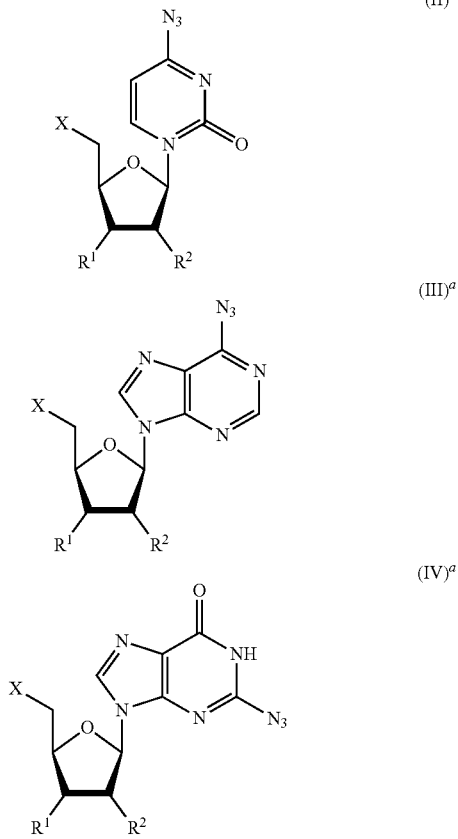

wherein X, $R^1$, $R^2$, $R^3$ and B are as defined herein, chemical, with electromagnetic radiation, with heat and/or with an electric current.

According to a further aspect of the invention, there is provided a process of preparing a compound of formula (II), (III) or (IV) as defined herein, which comprises reacting a compound of formula (VI):

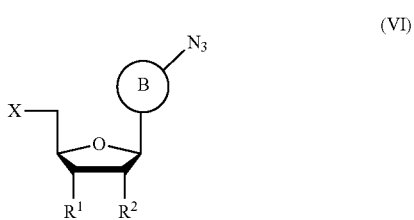

wherein X, $R^1$, $R^2$ and B are as defined herein, with a reducing agent.

BRIEF DESCRIPTION OF THE FIGURES

FIG. 6: Extent of deamination of N4-acetyl 2'-deoxycytidine (N4-acetyl dC) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. (A) Trace showing initial compound with mass of the primary peak shown, confirming the identity of the compound at ~2.1 min as N4-acetyl dC. (B) Time course of N4-acetyl dC incubated with nitrite solution as described above. Data shown as a series of LC chromatograms at 260 nm. There is a notable reduction in the peaks corresponding to dC (reduction product) or dU (deamination product), when compared to a dC standard incubated with nitrite solution (see FIG. 4). (C) N4-acetyl dC can be easily converted to dC. One such method involves treatment with aqueous 40% methylamine, which can be seen to result in loss of the N4-acetyl dC peak at 2.1 min and appearance of the dC peak at 1.05 minutes, as confirmed by mass in panel (D).

FIG. 7: Extent of deamination of N6-acetyl adenosine (N6-acetyl A) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. (A) Trace showing initial compound with mass of the primary peak shown, confirming the identity of the compound at ~1.8 min as N6-acetyl A. (B) Time course of N6-acetyl A incubated with nitrite solution as described above. Data shown as a series of LC chromatograms at 260 nm. While minor deacetylation is seen at 48 hours, no deamination product is detected. (C) N6-acetyl A can be easily converted to dC. One such method involves treatment with aqueous 40% methylamine, which can be seen to result in loss of the N6-acetyl A peak at 1.8 min and appearance of the A peak at 1.9 minutes, as confirmed with the extracted mass traces corresponding to the acetylated (310.50 extraction) and deacetylated (268.00 extraction) compound. (D) Another method to deacetylate N6-acetyl A is with potassium carbonate. Here, treatment with 50 mM aqueous potassium carbonate at room temperature afforded the deacetylated compound, again proven with the disappearance of the 310.50 peak and appearance of the 268.00 peak.

Figure 8A:
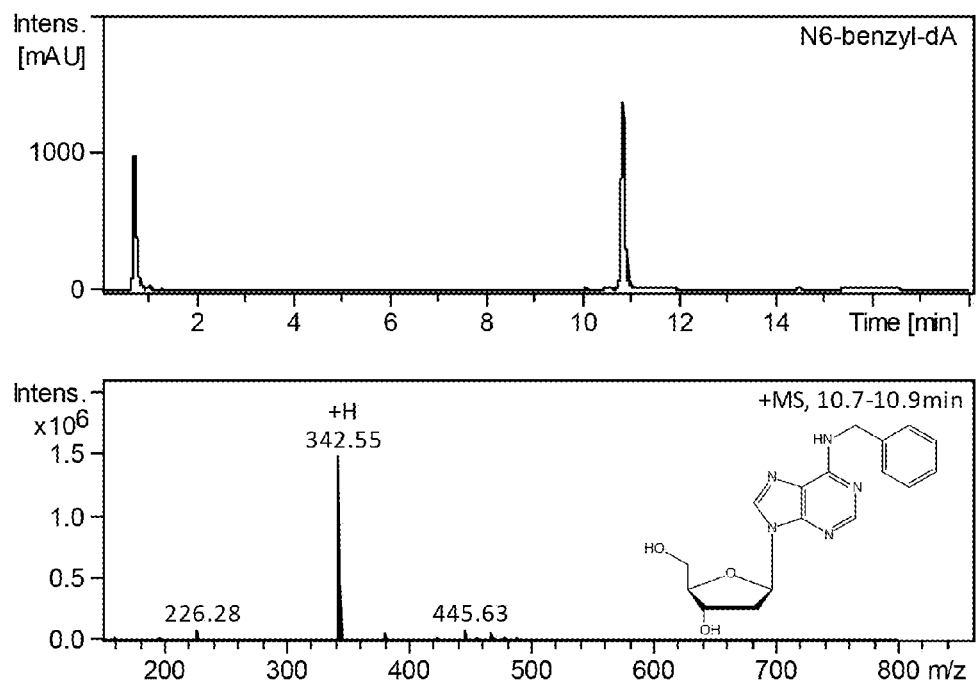
Figure 8B:
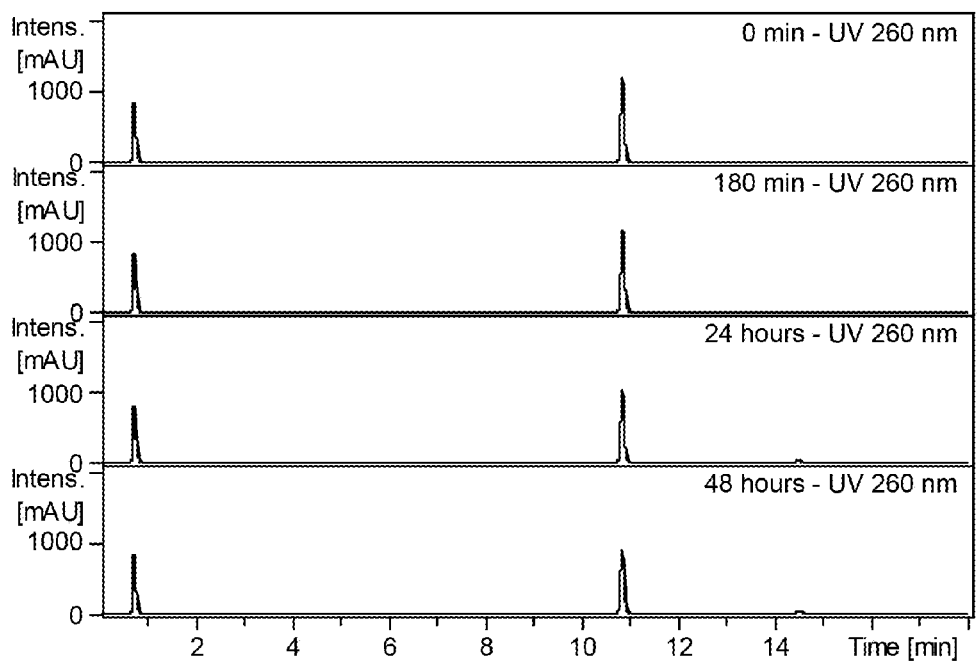
Figure 9A:
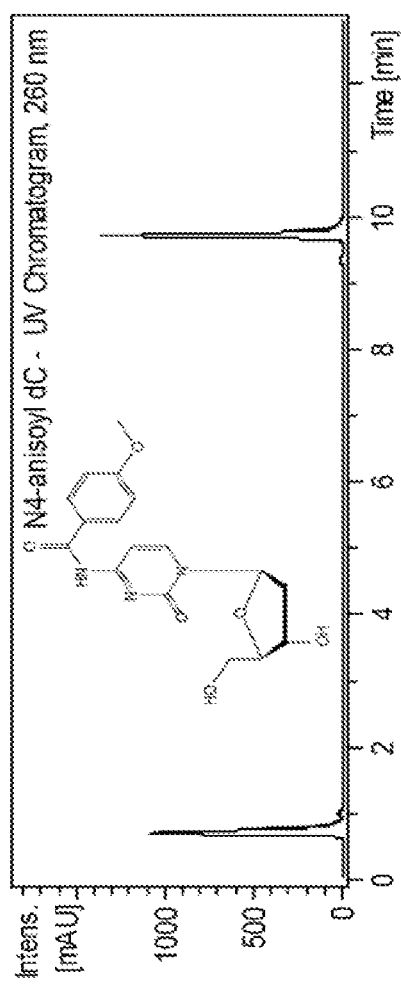
Figure 9B:
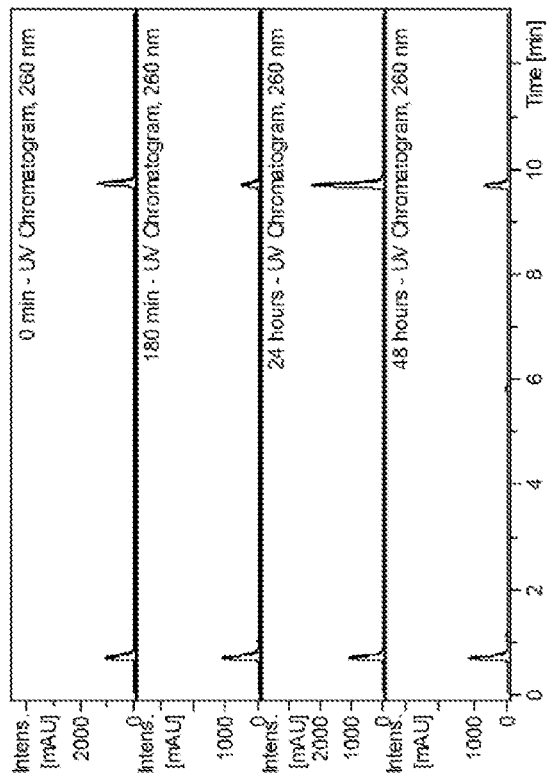
Figure 9C:
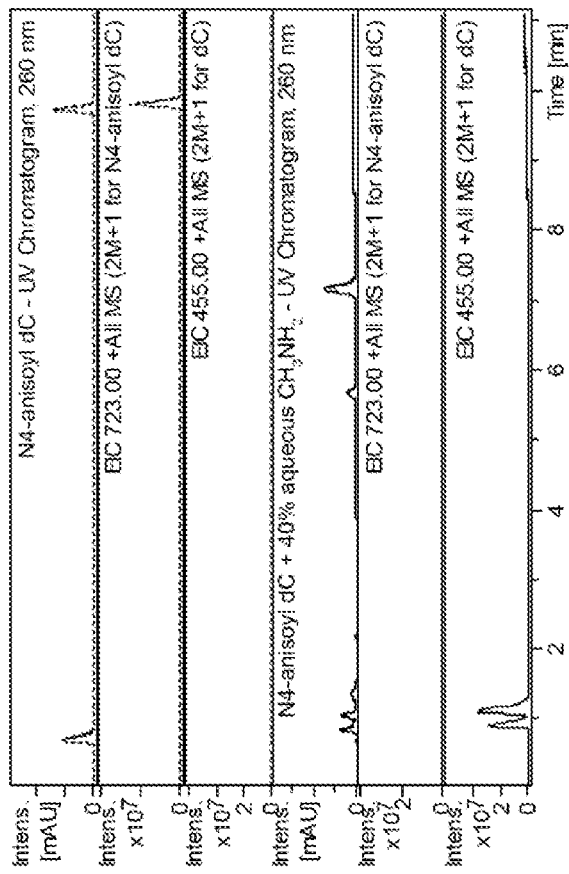
Figure 9D:
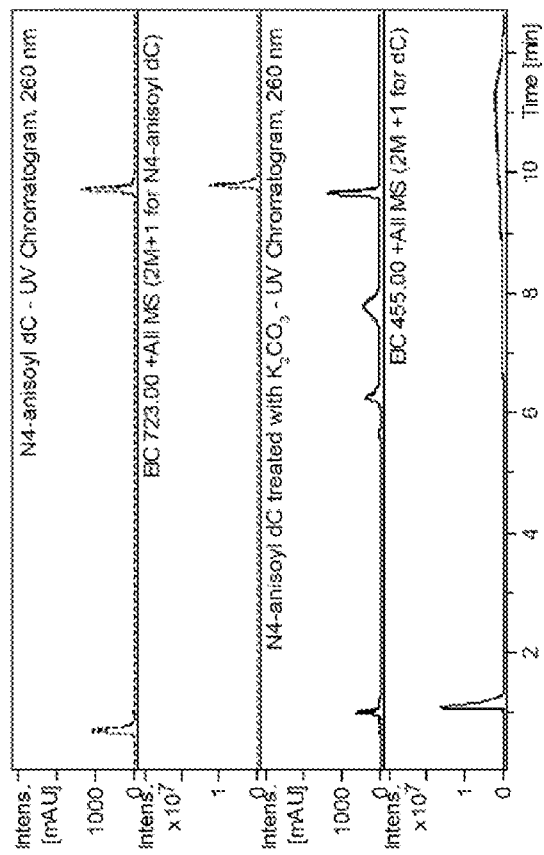

FIG. 8: Extent of deamination of N6-benzyl 2'-deoxyadenosine (N6-benzyl dA; 1 mM) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes followed by a hold for 5 minutes was run at 0.4 mL/min. (A) Trace showing initial compound with mass of the primary peak shown, confirming the identity of the compound at ~10.8 min as N6-benzyl dA. (B) Time course of N6-benzyl dC incubated with nitrite solution as described above. Data shown as a series of LC chromatograms at 260 nm. There is a notable absence of peaks corresponding to dA (debenzylated product) or deoxyinosine (dI; deamination product).

FIG. 9: Extent of deamination of N4-anisoyl 2'-deoxycytidine (N4-anisoyl dC) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. (A) Trace showing initial compound with mass of the primary peak shown, confirming the identity of the compound at ~9.8 min as N4-anisoyl dC. (B) Time course of N4-anisoyl dC incubated with nitrite solution as described above. Data shown as a series of LC chromatograms at 260 nm. There is a notable reduction in the peaks corresponding to dC (reduction product) or dU (deamination product), when compared to a dC standard incubated with nitrite solution (see FIG. 4). (C) N4-anisoyl dC can be easily converted to dC. One such method involves treatment with aqueous 40% methylamine, which can be seen to result in loss of the N4-anisoyl dC peak at ~9.8 min and appearance of the dC peak at 1.05 minutes, as confirmed with the extracted mass traces. (D) Another method to deacylate N4-anisoyl dC to dC involves treatment with potassium carbonate. Here, treatment with 50 mM aqueous potassium carbonate at room temperature afforded the deacylated compound dC.

Figure 10:
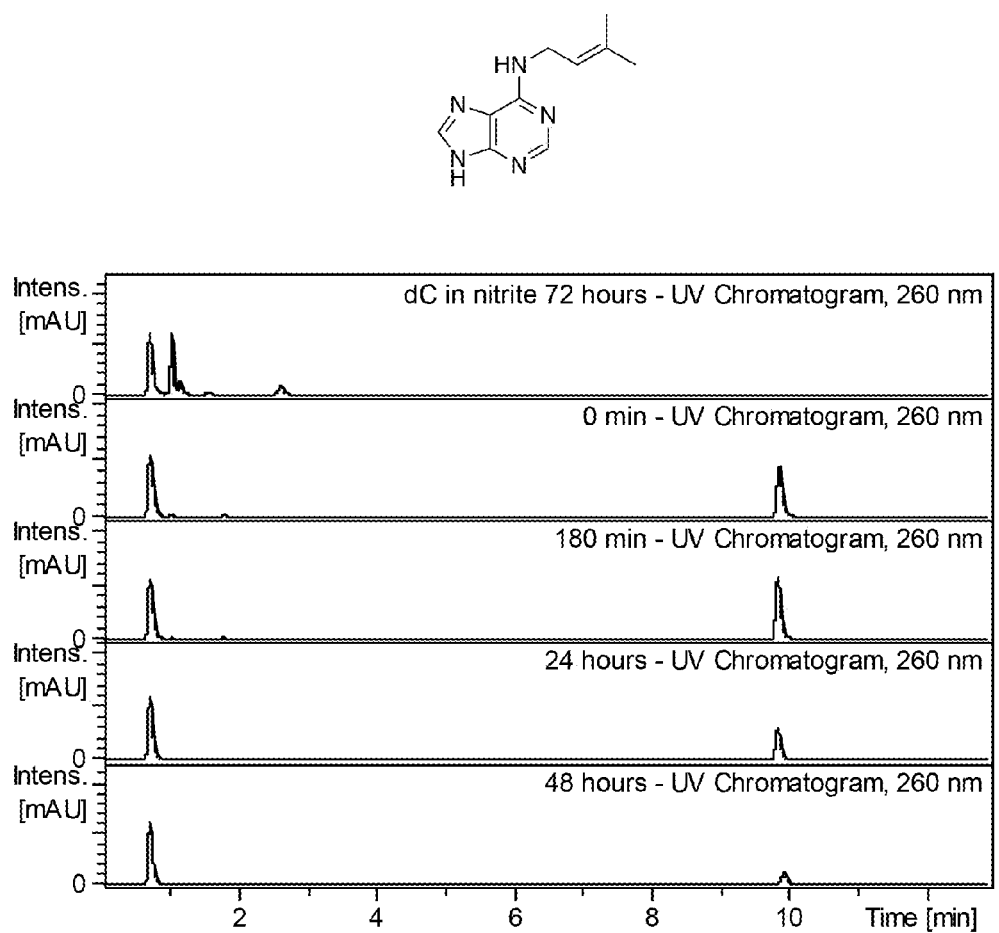

FIG. 10: Extent of deamination of N6-dimethylallylamino purine in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. Time course of N6-dimethylallylamino purine incubated with nitrite solution as described above. Data shown as a series of LC chromatograms at 260 nm. There is a notable absence of peaks corresponding to dA or dI.

Figure 11A:
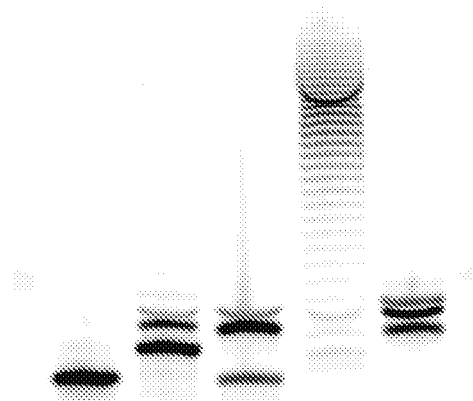
Figure 11B:
Figure 11C:
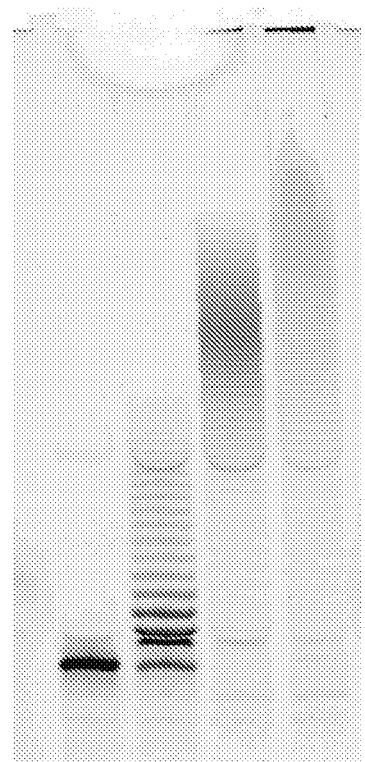
Figure 12A:
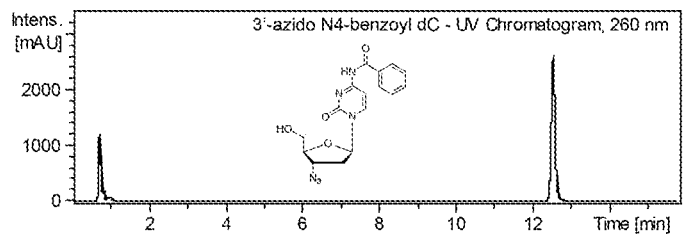
Figure 12B:
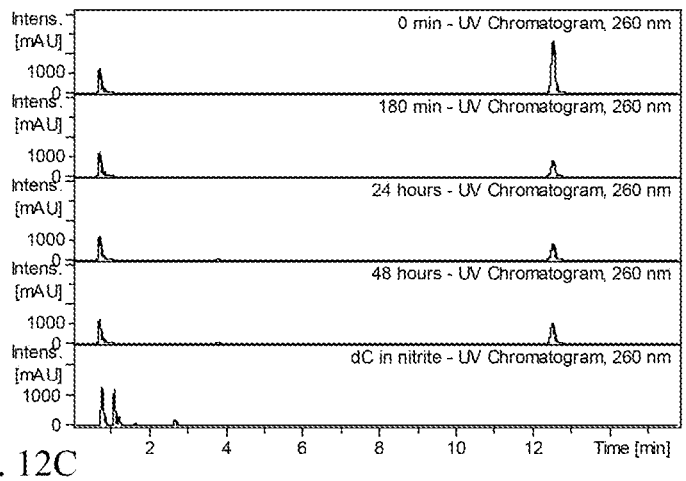
Figure 12C:
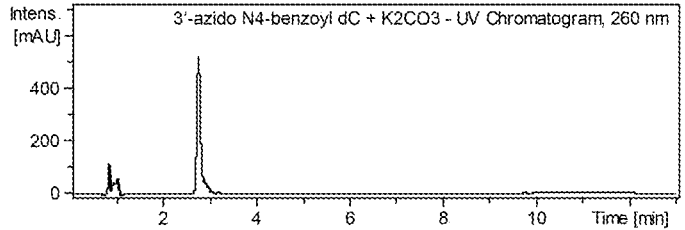
Figure 12C:
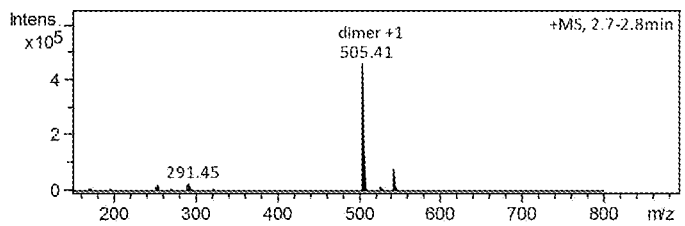

FIG. 11: Enzymatic incorporation of nucleoside 5'-triphosphates with amine-masking moieties. An engineered terminal deoxynucleotidyl transferase was incubated for 10 minutes at 37° C. in an appropriate buffer containing cobalt chloride and a DNA primer with a 5'-fluorophore as well as the following nucleoside 5'-triphosphates: (A) Lane 1: No extension control; Lane 2: N6-benzyl-dATP; Lane 3: N6-benzyl-rATP; Lane 4: N6-methyl-dATP; Lane 5: N6-methyl-rATP; (B) Lane 1: No extension control; Lane 2: 3'-O-acetyl-N4-benzoyl-dCTP; (C) Lane 1: No extension control; Lane 3: N6-benzoyl-dATP; Lane 4: N4-benzoyl-dCTP. Reactions were analyzed by standard denaturing polyacrylamide gel electrophoresis (TBE buffer) and imaged with a fluorescent scanner.

FIG. 12: Extent of deamination of 3'-azido N4-benzoyl 2'-deoxycytidine (1 mM) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes followed by a hold for 5 minutes was run at 0.4 mL/min. (A) Trace showing initial compound with mass of the primary peak shown, confirming the identity of the compound at ~12.5 min as 3'-azido N4-benzoyl 2'-deoxycytidine. (B) Time course of 3'-azido N4-benzoyl 2'-deoxycytidine incubated with nitrite solution as described above. Data shown as a series of LC chromatograms at 260 nm. There is a notable absence of peaks corresponding to dc (deacylatedproduct) or deoxyinosine (deamination product)—which can be seen in the bottom trace showing a dC incubation with nitrite. (C) Treatment of 3'-azido N4-benzoyl 2'-deoxycytidine with potassium carbonate yields 3'-azido dC.

DETAILED DESCRIPTION OF THE INVENTION

According to a first aspect of the invention, there is provided the use of an amine masked derivative of a nitrogenous heterocycle, such as adenine, guanine, cytosine, isoguanine, isocytosine and 2,6-diaminopurine in a method of enzymatic nucleic acid synthesis.

According to a further aspect of the invention which may be mentioned, there is provided the use of an amine masked derivative of a nitrogenous heterocycle, such as adenosine, guanosine, and cytidine, in a method of enzymatic nucleic acid synthesis.

References herein to a derivative of adenosine, guanosine and cytidine refer to deoxy derivatives thereof (i.e. deoxyadenosine, deoxyguanosine and deoxycytidine) and the phosphated derivatives thereof (i.e. adenosine monophosphate, adenosine diphosphate, adenosine triphosphate, guanosine monophosphate, guanosine diphosphate, guanosine triphosphate, cytidine monophosphate, cytidine diphosphate, cytidine triphosphate and all the deoxyribose versions thereof).

According to a further aspect of the invention, there is provided the use of a compound of formula (I):

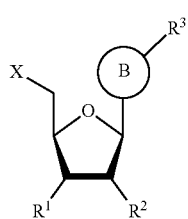

(I)

wherein:

$R^1$ represents a moiety capable of being unmasked to reveal a hydroxyl group, including —H, —OH, —ONH$_2$, —ONC(CH$_3$)$_2$, —OCH$_2$N$_3$, —OCH$_2$CHCH$_2$, —OPO$_3^{2-}$, —OCH$_2$SSCH$_2$CH$_3$, —OCOCH$_3$, —OCH$_2$CH$_2$CN, —O-methoxyethyl, —O-alkyl, or —O-alkoxy;

$R^2$ represents —H, —OH, —ONH$_2$, —ONC(CH$_3$)$_2$, —OCH$_2$N$_3$, —OCH$_2$CHCH$_2$, —OPO$_3^{2-}$, —OCH$_2$SSCH$_2$CH$_3$, —OCOCH$_3$, —OCH$_2$CH$_2$CN, —O-methoxyethyl, —O-alkyl, or —O-alkoxy or any other molecular moiety;

X represents an —OH group or one or more phosphate, phosphorothioate, boranophosphate or imidophosphate groups, or any combination thereof, wherein said group is capable of endowing competence for enzymatic addition;

$R^3$ represents an amine masking group, wherein said amino group would be involved in hydrogen bond base-pairing with a complementary base and deamination of said amino group could result in altered hydrogen bonding with a complementary base; and B represents a nitrogenous heterocycle;

in a method of enzymatic nucleic acid synthesis.

According to a further aspect of the invention which may be mentioned, there is provided the use of a compound of formula (I):

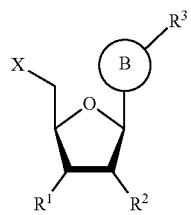

(I)

wherein:

$R^1$ and $R^2$ independently represent —H, —OH, —ONH$_2$, —ONC(CH$_3$)$_2$, —OCH$_2$N$_3$, —OCH$_2$CHCH$_2$, —O-methoxyethyl, —O-alkyl, —O-alkoxy, cyanoethyl, a thiol or a suitable hydroxy protecting group;

X represents an —OH group or one or more phosphate, phosphorothioate, boranophosphate or imidophosphate groups, or any combination thereof;

$R^3$ represents an amine masking group, wherein said amino group is involved in hydrogen bond base-pairing with a complementary base; and B represents a nitrogenous heterocycle;

in a method of enzymatic nucleic acid synthesis.

Enzymatic nucleic acid synthesis is defined as any process in which a nucleotide is added to a nucleic acid strand through enzymatic catalysis in the presence or absence of a template.

For example, a method of enzymatic nucleic acid synthesis could include non-templated de novo nucleic acid synthesis utilizing a PolX family polymerase, such as terminal deoxynucleotidyl transferase, and reversibly terminated 2'-deoxynucleoside 5'-triphosphates or ribonucleoside 5'-triphosphate. Another method of enzymatic nucleic acid synthesis could include templated nucleic acid synthesis, including sequencing-by-synthesis. Reversibly terminated enzymatic nucleic acid synthesis is defined as any process in which a reversibly terminated nucleotide is added to a nucleic acid strand through enzymatic catalysis in the presence or absence of a template. A reversibly terminated nucleotide is a nucleotide containing a chemical moiety that blocks the addition of a subsequent nucleotide. The deprotection or removal of the reversibly terminating chemical moiety on the nucleotide by chemical, electromagnetic, electric current, and/or heat allows the addition of a subsequent nucleotide via enzymatic catalysis. Thus, in one embodiment, the method of enzymatic nucleic acid synthesis is selected from a method of reversibly terminated enzymatic nucleic acid synthesis and a method of templated and non-templated de novo enzymatic nucleic acid synthesis.

The compound of formula (I) contains three synergistic components which may be summarized as follows:

(i)—The $R^3$ group. $R^3$ is typically a chemical moiety on the nitrogenous heterocycle that can be unmasked to reveal an amino (—NH$_2$) group;

(ii)—The $R^1$ group. $R^1$ is typically a chemical moiety at the 3'-position on the sugar that can be unmasked to reveal a hydroxyl (—OH) group; and (iii)—The X group. X is typically a chemical moiety endowing competence for enzymatic addition (e.g., 5'-triphosphate group).

Without being bound by theory, it is believed that the combination of $R^1$, $R^3$ and X result in nucleotide analogs that protect the amino group in component (i) from mutation during the method of enzymatic nucleic acid synthesis described herein. Specifically, a method of enzymatic nucleic acid synthesis would involve nucleotide analogs that have characteristic $R^3$, X, and $R^1$, where $R^1$ is fixed as an —$ONH_2$ group.

In one embodiment, $R^1$ and $R^2$ independently represent —H, —OH, —$ONH_2$, —$ONC(CH_3)_2$, —$OCH_2N_3$, —$OCH_2CHCH_2$, —$OPO_3^{2-}$, —$OCH_2SSCH_2CH_3$, —$OCOCH_3$, —$OCH_2CH_2CN$, —O-methoxyethyl, —O-alkyl, or —O-alkoxy or a suitable hydroxyl protecting group.

In one embodiment, the compound of formula (I) is selected from:

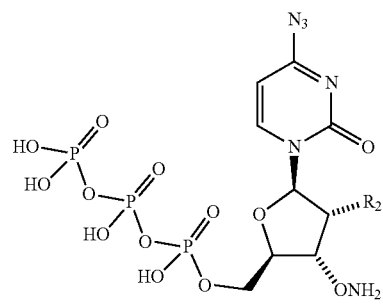

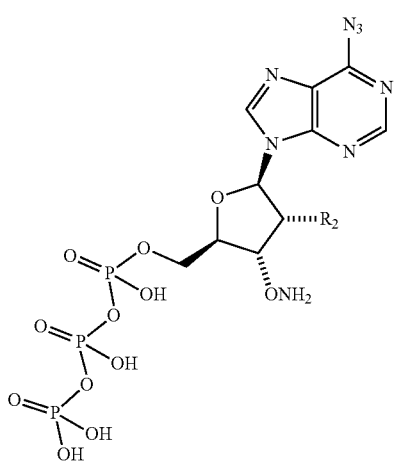

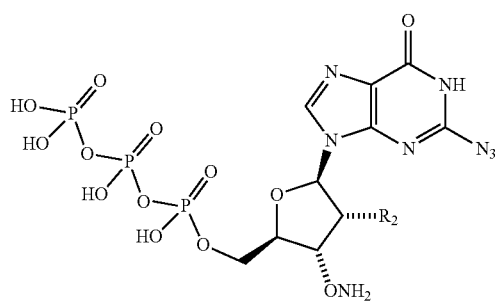

where $R^2$ is as defined herein, such as —OH or —H. In one embodiment, $R^2$ is H.

In one embodiment, the compound of formula (I) is a compound of formula (I)$^b$:

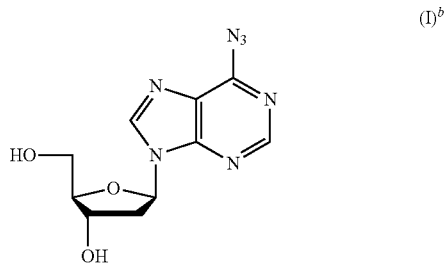

Figure 1A:
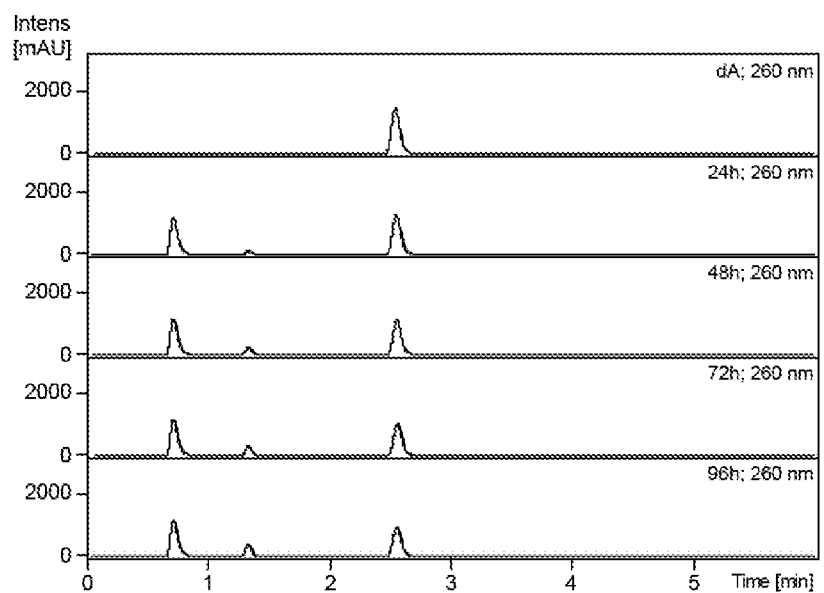
FIG. 1: A time course showing the extent of deamination of 2'-deoxyadenosine (1 mM) in the presence of sodium nitrite (700 mM), sodium acetate, pH 5.5 (1 M) at room temperature. (A) LC-MS was performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-40% B in 10 minutes was run at 0.5 mL/min. Data is shown as a series of LC chromatograms at 260 nm. The ~2.6 min peak corresponds to 2'-deoxyadenosine and the peak at ~1.3 min corresponds to 2'-deoxyinosine (oxidative deamination product). (B) Plot of deamination percent over time. (C) Oxidative deamination reaction shown below converting 2'-deoxyadenosine to 2'deoxyinosine.
Figure 1B:
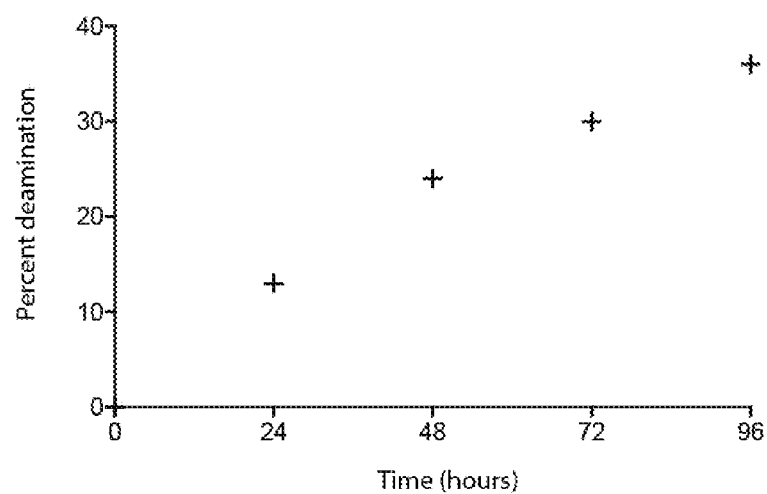
Figure 1C:
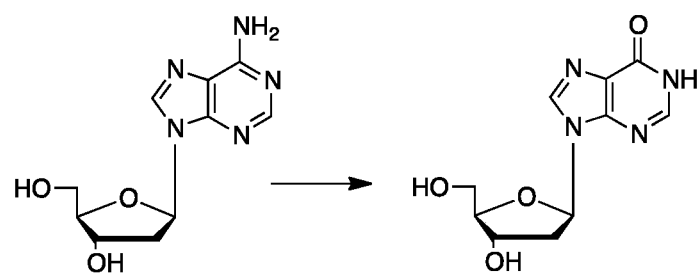
Figure 2:
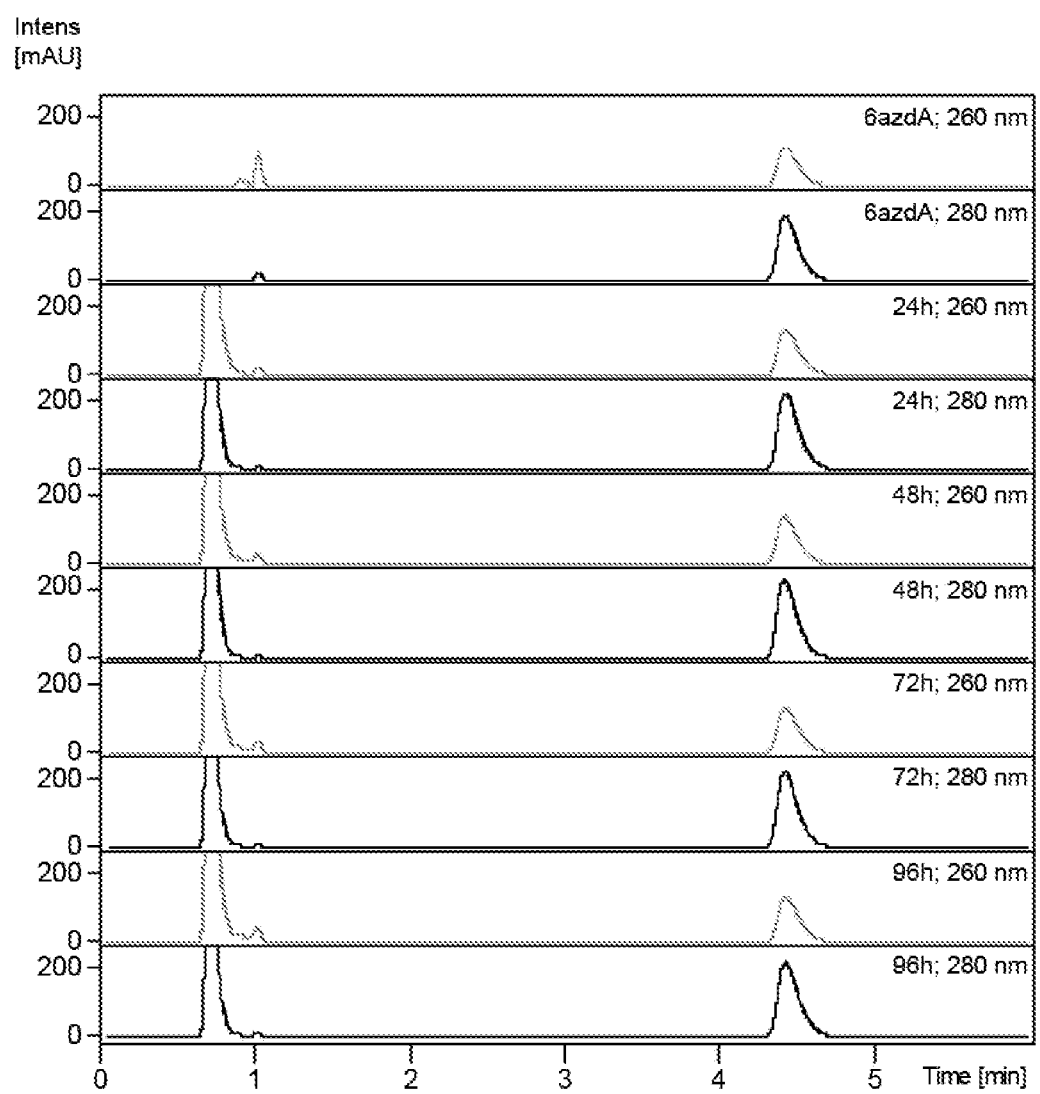
FIG. 2: Time course of the extent of deamination of N6-azido 2'-deoxyadenosine (0.5 mM) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-40% B in 10 minutes was run at 0.5 mL/min. Data shown as a series of LC chromatograms at two wavelengths for each time point as labeled above. The peak at ~4.5 min retention time corresponds with 6-azido 2'-deoxyadenosine. There is a notable absence of peaks at ~2.6 min (2'-deoxyadenosine) or ~1.3 min (2'-deoxyinosine; oxidative deamination product).
Figure 3:
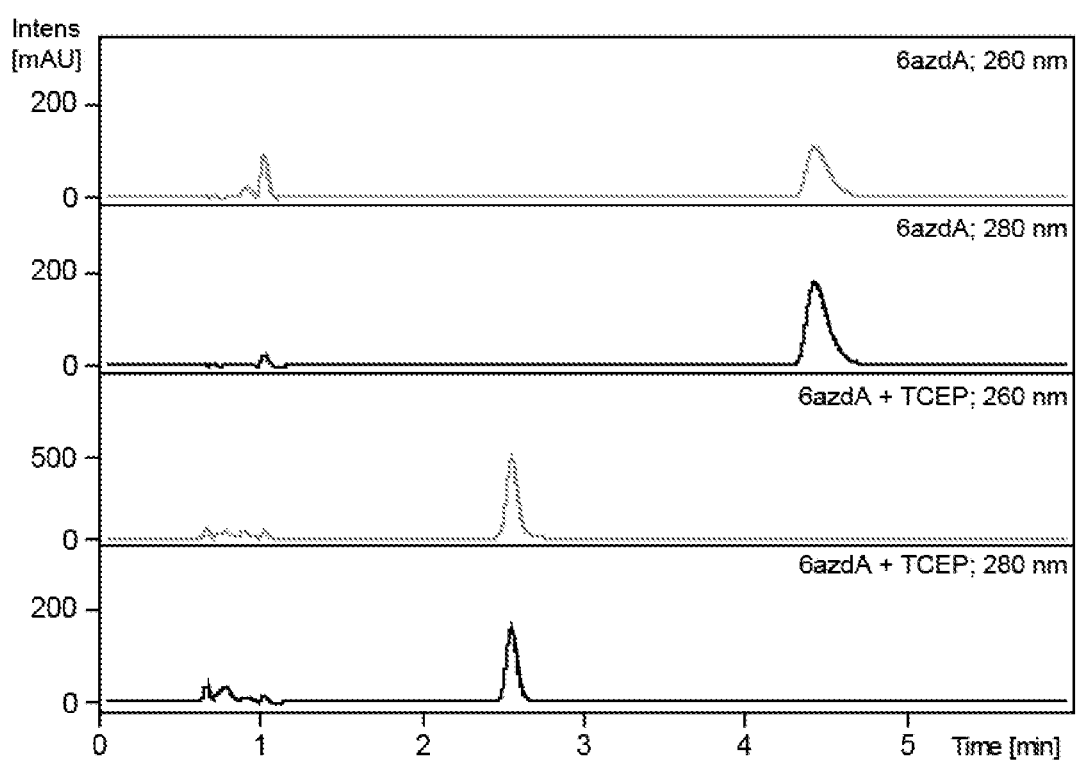
FIG. 3: Exposure of 6-azido 2'-deoxyadenosine (4.5 min retention time) to TCEP results in quantitative conversion to 2'-deoxyadenosine (2.6 min retention time) as analyzed by LC-MS. Analysis was performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-40% B in 10 minutes was run at 0.5 mL/min.

The compound of formula (I)$^b$ is known chemically as N6-azido 2'-deoxyadenosine. Upon exposure of the compound of formula (I)$^b$ to sodium nitrite, no conversion to 2'-deoxyinosine was observed, as shown in FIG. 2. Conveniently, upon exposure to TCEP or another reducing agent, the compound of formula (I)$^b$ is easily converted to 2'-deoxyadenosine, as shown in FIG. 3.

In one embodiment, the compound of formula (I) is a compound of formula (I)$^b$:

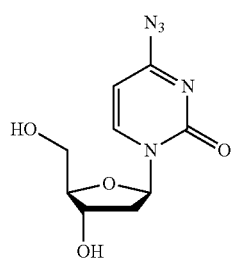

Figure 4A:
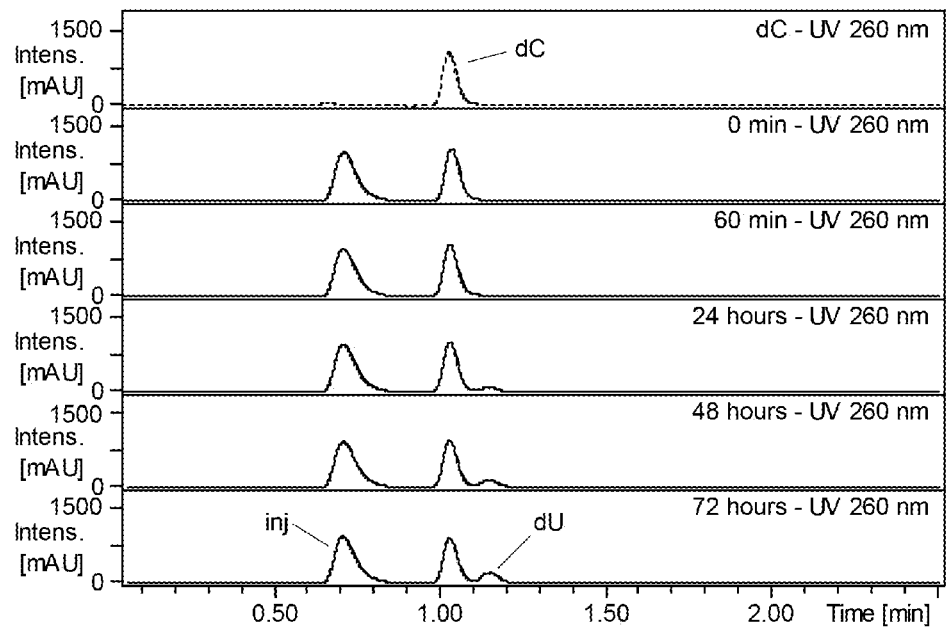
FIG. 4: A time course showing the extent of deamination of 2'-deoxycytosine (1 mM) in the presence of sodium nitrite (700 mM), sodium acetate, pH 5.5 (1 M) at room temperature. (A) LC-MS was performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. Data is shown as a series of LC chromatograms at 260 nm. The ~1.05 min peak corresponds to 2'-deoxycytidine and the peak at ~1.15 min corresponds to 2'-deoxyuridine (oxidative deamination product). (B) Plot of deamination percent over time. (C) Oxidative deamination reaction shown below converting 2'-deoxycytidine (dC) to 2'-deoxyuridine (dU).
Figure 4B:
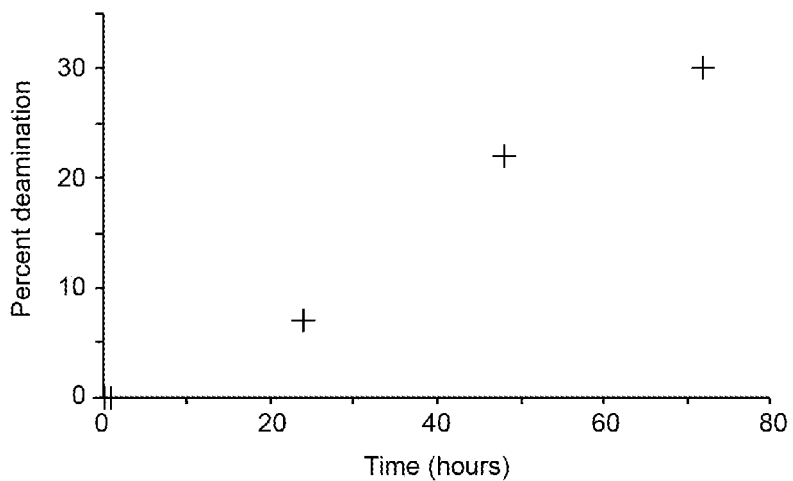
Figure 4C:
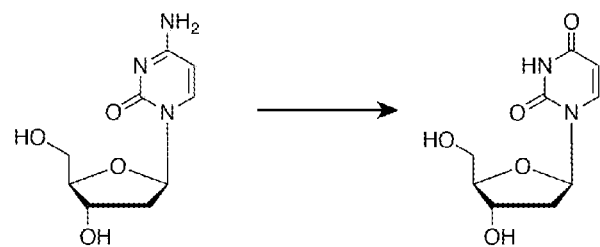
Figure 5A:
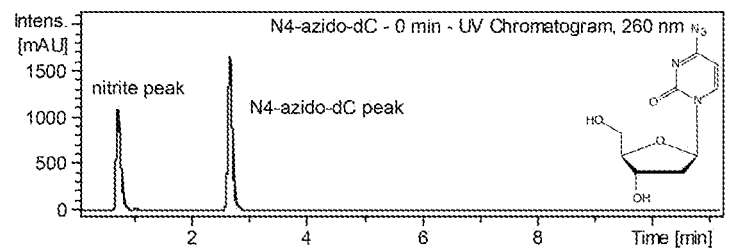
FIG. 5: Extent of deamination of N4-azido 2'-deoxycytidine (N4-azido dC; 1 mM) in the presence of sodium nitrite (700 mM), sodium acetate, pH 5.5 (1 M) at room temperature as analyzed by LC-MS performed on a Bruker amaZon system, with a Synergi Polar RP column. Solvents were A (20 mM ammonium acetate, pH 4.6) and B (20 mM ammonium acetate, pH 4.6 [5%]/acetonitrile [95%]). A gradient from 5-25% B in 10 minutes was run at 0.4 mL/min. (A) Trace showing initial compound with mass of the primary peak shown, confirming the identity of the compound at ~2.7 min as N4-azido dC. (B) Time course of N4-azido dC incubated with nitrite solution as described above. Data shown as a series of LC chromatograms at 260 nm. There is a notable absence of peaks corresponding to dC (reduction product) or dU (deamination product), which can be seen in the first trace from a dC standard incubated with nitrite solution. (C) N4-azido dC can be easily converted to dC by treatment with a reducing agent. Here, incubation with TCEP led to quantitative conversion of N4-azido dC to dC.
Figure 5A:
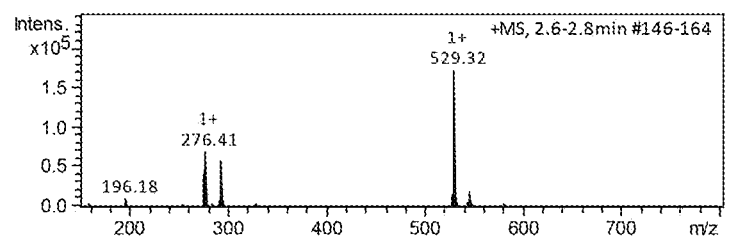
Figure 5B:
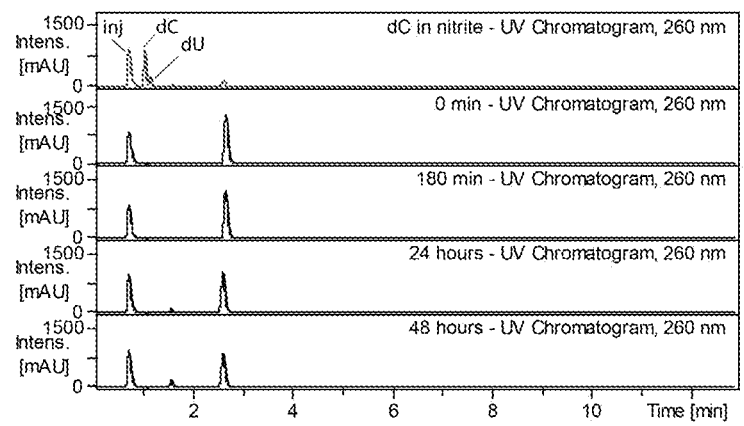
Figure 5C:
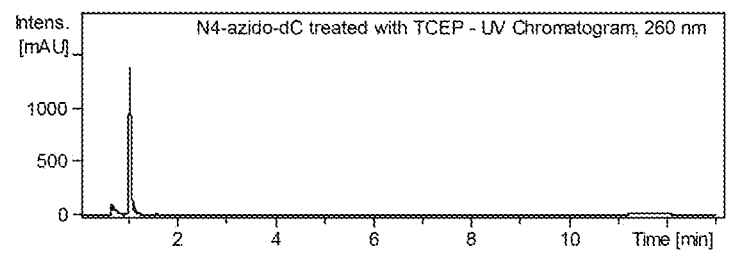
Figure 5C:
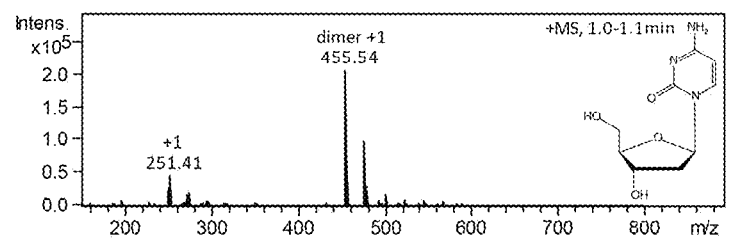
Figure 6A:
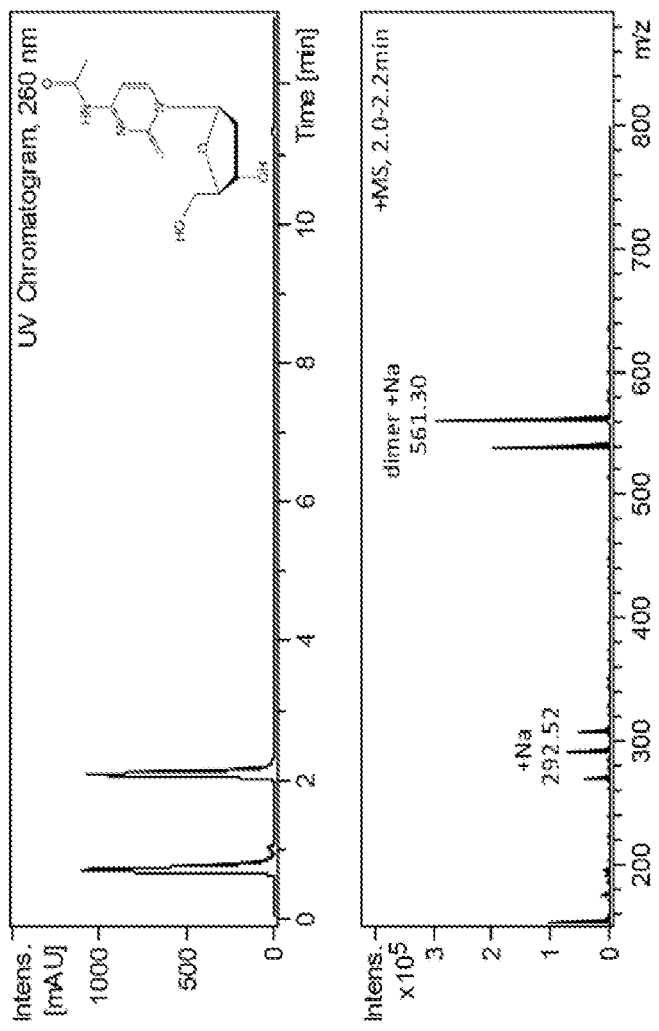
Figure 6B:
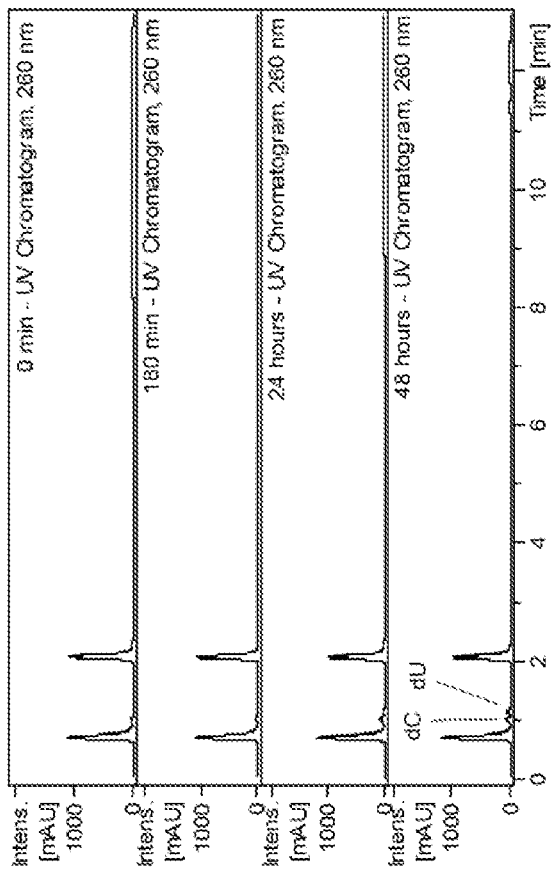
Figure 6C:
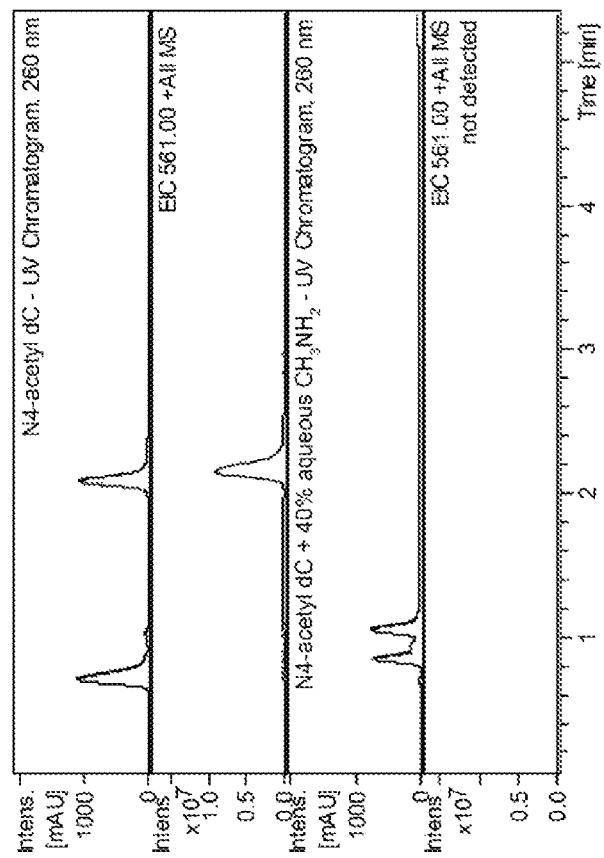
Figure 6D:
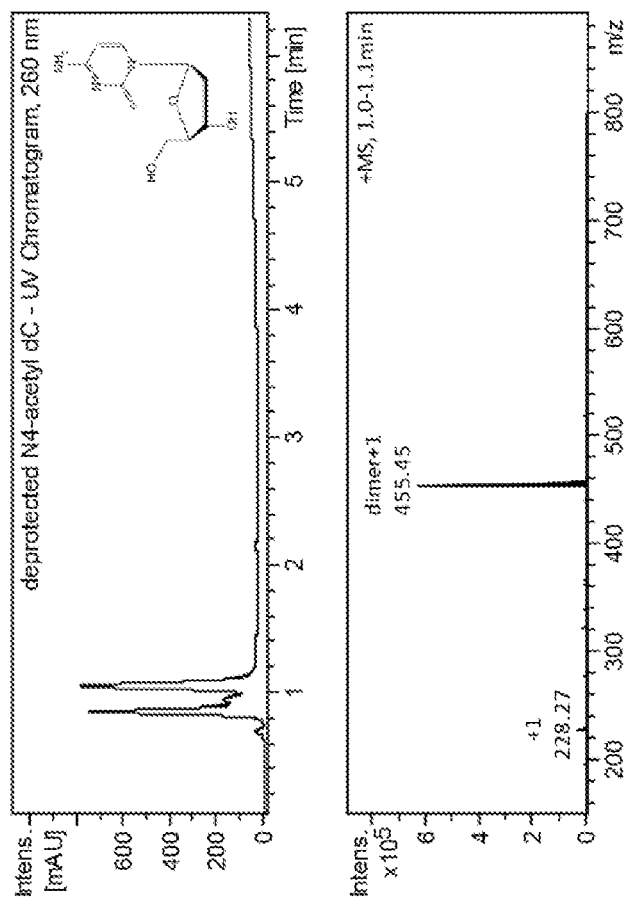
Figure 7A:
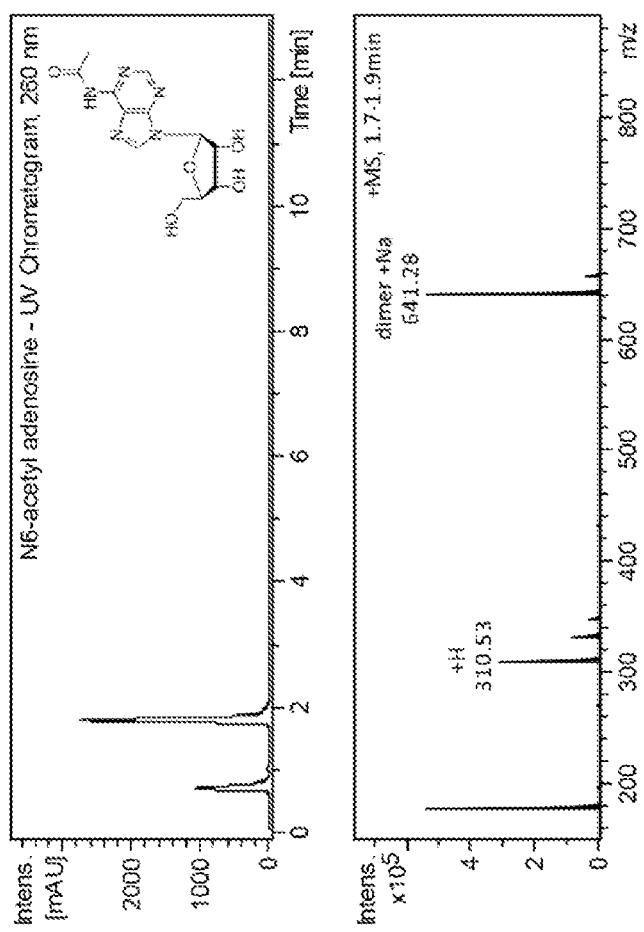
Figure 7B:
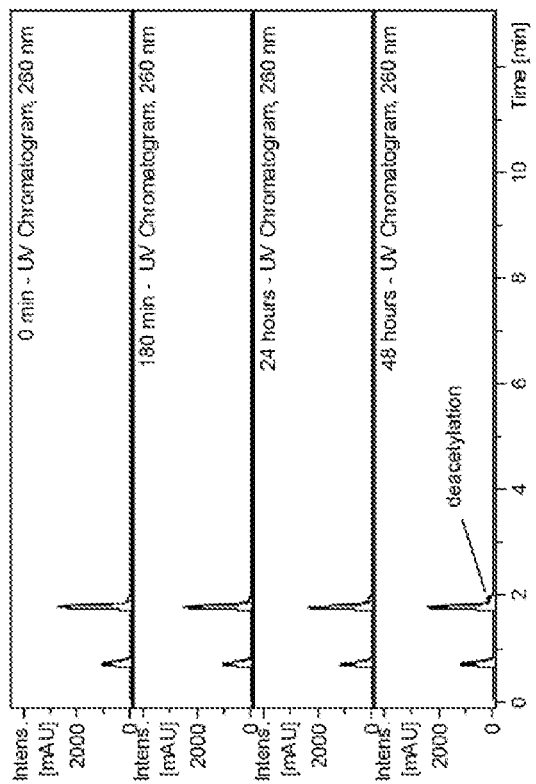
Figure 7C:
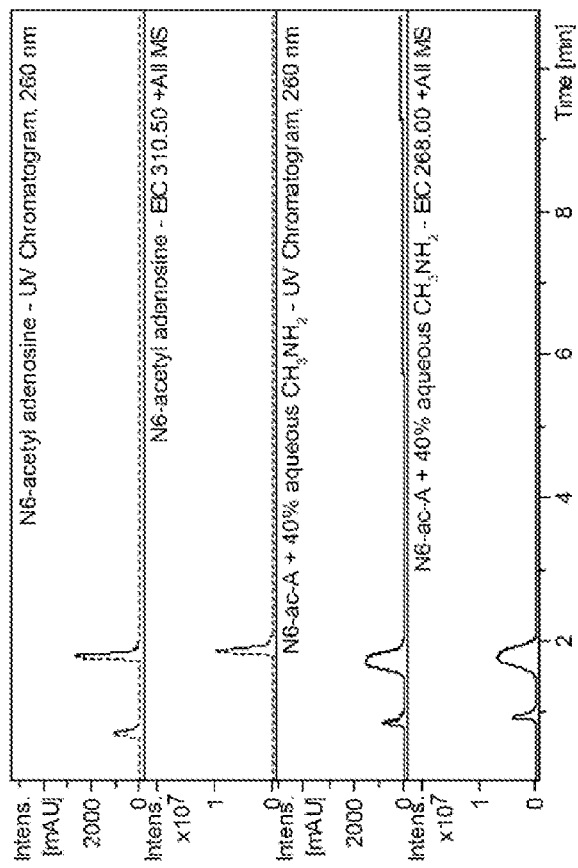
Figure 7D:
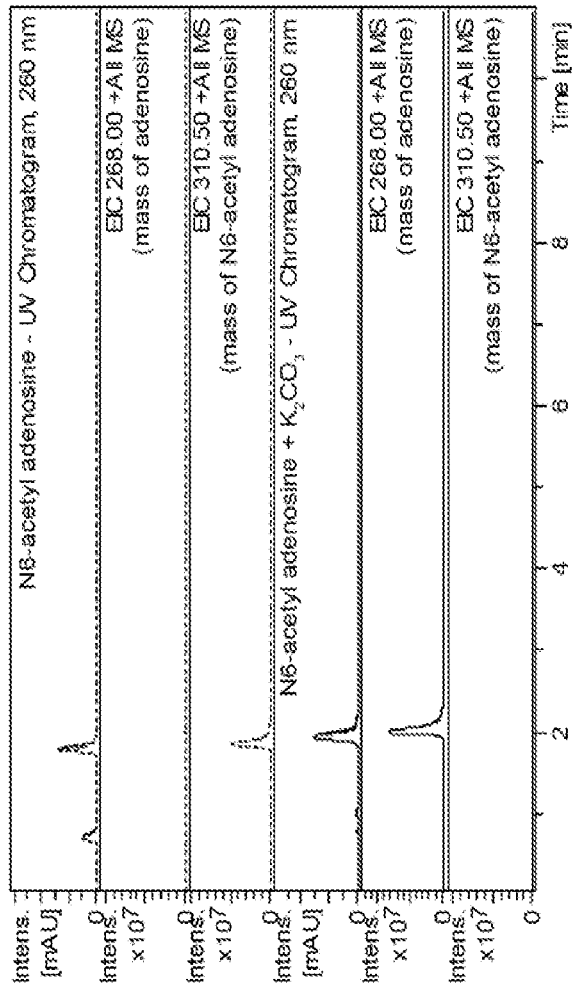

The compound of formula (I)$^c$ is known chemically as N4-azido 2'-deoxycytidine. Upon exposure of the compound of formula (I)$^c$ to sodium nitrite, no conversion to 2'-deoxyuracil was observed, as shown in FIG. 4. Conveniently, upon exposure to TCEP or another reducing agent, the compound of formula (I)$^c$ is easily converted to 2'-deoxycytidine, as shown in FIG. 5. Thus, the present invention provides the advantage of providing a solution to the problem of oxidative deamination of adenine, guanine and cytosine in the presence of reagents such as sodium nitrite under acidic conditions.

In one embodiment, the compound of formula (I) is a compound of formula (I)$^d$:

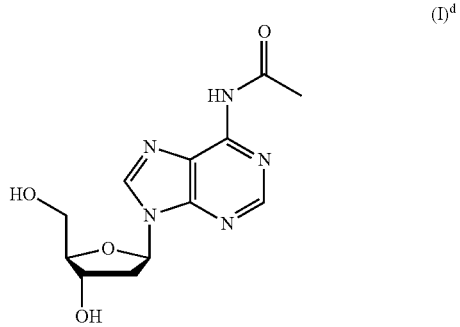

The compound of formula (I)$^d$ is known chemically as N6-acetyl 2'-deoxyadenosine. Upon exposure of the compound of formula (I)$^d$ to sodium nitrite, no conversion to 2'-deoxyinosine was observed, as shown in FIG. 7. Conveniently, upon exposure to 40% aqueous methylamine, or potassium carbonate, or ammonium hydroxide, or ammonia (for instance in ethanol) or other appropriate reagents, the compound of formula (I)$^d$ is easily converted to 2'-deoxyadenosine, as shown in FIG. 7.

In one embodiment, the compound of formula (I) is a compound of formula (I)$^e$:

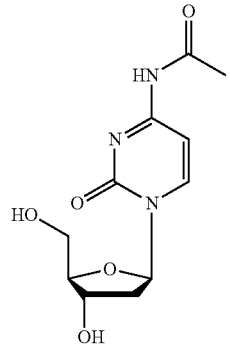

The compound of formula (I)$^e$ is known chemically as N4-acetyl 2'-deoxycytidine. Upon exposure of the compound of formula (I)$^e$ to sodium nitrite, no conversion to 2'-deoxyuracil was observed, as shown in FIG. 6. Conveniently, upon exposure to methylamine or other bases, the compound of formula (I)$^e$ is easily converted to 2'-deoxycytidine, as shown in FIG. 6. Thus, the present invention provides the advantage of providing a solution to the problem of oxidative deamination of adenine, guanine and cytosine in the presence of reagents such as sodium nitrite under acidic conditions.

In one embodiment, the compound of formula (I) is a compound of formula (I)$^f$:

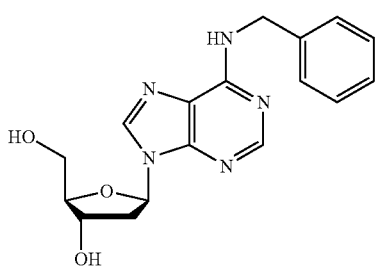

The compound of formula (I)$^f$ is known chemically as N6-benzyl 2'-deoxyadenosine. Upon exposure of the compound of formula (I)$^f$ to sodium nitrite, no conversion to 2'-deoxyinosine was observed, as shown in FIG. 8. Conveniently, upon treatment with hydrogen in the presence of a suitable catalyst (such as palladium or nickel), the compound of formula (I)$^f$ is easily converted to 2'-deoxyadenosine. The triphosphate form of species (I)$^f$ can act as a substrate for terminal transferase enzymes in a DNA synthesis process as shown in FIG. 11. Thus, the present invention provides a solution to the problem of oxidative deamination and offers utility in a method of enzymatic DNA synthesis.

In one embodiment, the compound of formula (I) is a compound of formula (I)$^g$:

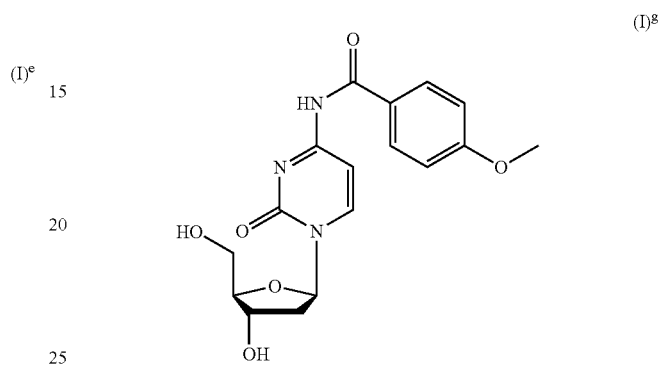

The compound of formula (I)$^g$ is known chemically as N4-anisoyl 2'-deoxycytidine. Upon exposure of the compound of formula (I)$^g$ to sodium nitrite, no conversion to 2'-deoxyinosine was observed, as shown in FIG. 9. Conveniently, upon treatment with methylamine or potassium carbonate, or another suitable base or reagent, the compound of formula (I)$^g$ is easily converted to 2'-deoxycytidine as shown in FIG. 9. The identical chemistry is appropriate for benzoyl moieties, as found in N4-benzoyl 2'-deoxycytidine and N6-benzoyl 2'-deoxyadenosine.

In one embodiment, the compound of formula (I) is a compound of formula (I)$^h$:

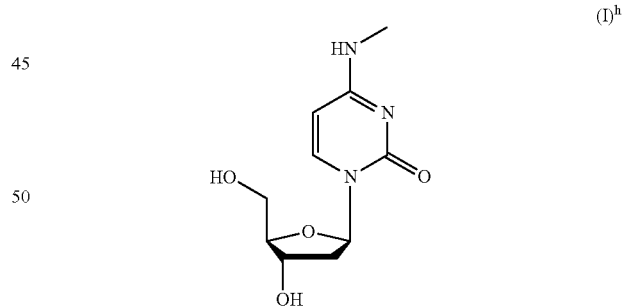

The compound of formula (I)$^h$ is known chemically as N4-methyl 2'-deoxycytidine. As shown here, secondary amines are protected from oxidative deamination induced by nitrite solutions. Thus N-methyl would be an appropriate protecting group. Exocyclic N-methyl can be conveniently removed by treatment with demethylating enzymes such as AlkB (D. Li, et al., Chem. Res. Toxicol. 26 (2013) 1182-1187).

In one embodiment, the compound of formula (I) is a compound of formula (I)$^i$:

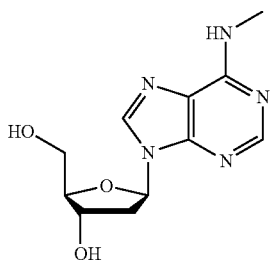

(I)^i

The compound of formula (I)^i is known chemically as N6-methyl 2'-deoxyadenosine. As shown here, secondary amines are protected from oxidative deamination induced by nitrite solutions. Thus N-methyl would be an appropriate protecting group. Exocyclic N-methyl can be conveniently removed by treatment with demethylating enzymes such as AlkB (D. Li, et al., Chem. Res. Toxicol. 26 (2013) 1182-1187). The triphosphate form of species (I)^i can act as a substrate for terminal transferase enzymes in a DNA synthesis process as shown in FIG. 11. Thus, the present invention provides a solution to the problem of oxidative deamination and offers utility in a method of enzymatic DNA synthesis.

In one embodiment, the compound of formula (I) is a compound of formula (I)^j:

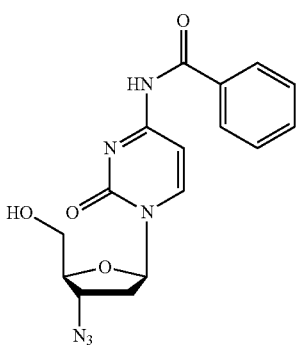

(I)^j

The compound of formula (I)^j is known chemically as 3'-azido N4-benzoyl 2'-deoxycytidine. Upon exposure of the compound of formula (I)^j to sodium nitrite, no conversion to 3'-azido 2'-deoxyinosine was observed, as shown in FIG. 12. Conveniently, upon treatment with methylamine or potassium carbonate, or another suitable base or reagent, the compound of formula (I)^j is easily converted to 3'-azido 2'-deoxycytidine as shown in FIG. 12. The triphosphate species of a closely related compound to (I)^j, N4-benzoyl 2'-deoxycytidine triphosphate, is accepted as a substrate by terminal transferase enzyme in a DNA synthesis process as shown in FIG. 11. Thus, the present invention provides a solution to the problem of oxidative deamination and offers utility in a method of enzymatic DNA synthesis.

In one embodiment, X represents an —OH group. In an alternative embodiment, X represents a triphosphate group. The triphosphate group of this embodiment has the advantage of being most commonly utilized with nucleotidyl transferases (e.g., polymerases) or any chemical moieties allowing addition to a nucleic acid molecule through enzymatic or chemical catalysis.

References herein to "amine" refer to a —NH$_2$ group.

References herein to an "amine masking group" refer to any chemical group which is capable of generating or "unmasking" an amine group which is involved in hydrogen bond base-pairing with a complementary base. Most typically the unmasking will follow a chemical reaction, most suitably a simple, single step chemical reaction. In one embodiment, the hydrogen bond base-pairing is selected from: Watson-Crick, Hoogsteen, or alternative/expanded genetic code base pairing.

Examples of suitable amine masking groups for R$^3$ include azide (—N$_3$), benzoylamine (N-benzoyl or —NHCOPh), N-methyl (—NHMe), isobutyrylamine, dimethylformamidylamine, 9-fluorenylmethyl carbamate, t-butyl carbamate, benzyl carbamate, acetamide (N-acetyl or —NHCOMe), trifluoroacetamide, pthlamide, benzylamine (N-benzyl or —NH—CH$_2$-phenyl), triphenylmethylamine, benxylideneamine, tosylamide, isothiocyanate, N-allyl (such as N-dimethylallyl (—NHCH$_2$—CH═CH$_2$)) and N-anisoyl (—NHCOPh-OMe), such as azide (—N$_3$), N-acetyl (—NHCOMe), N-benzyl (—NH—CH$_2$-phenyl), N-anisoyl (—NHCOPh-OMe), N-methyl, (—NHMe), N-benzoyl (—NHCOPh), N-dimethylallyl (—NHCH$_2$—CH═CH$_2$).

In one embodiment, B represents a nitrogenous heterocycle selected from a purine or pyrimidine, or derivative thereof. In a further embodiment, B and R3 can be combined into the following molecular structures, where the nitrogenous heterocycle is connected to the (deoxy)ribose 1' position of the compound of formula (I):

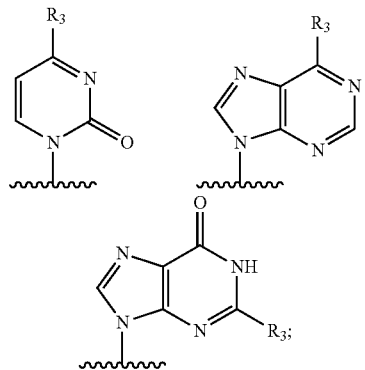

In a further embodiment, R$^3$ represents an azide (—N$_3$) group and B is selected from:

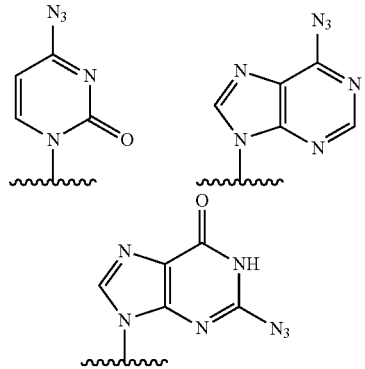

The term 'azide' or 'azido' used herein refers to an —$N_3$, or more specifically, an —N=$N^+$=$N^-$ group. It will also be appreciated that azide extends to the presence of a tetrazolyl moiety. The "azide-tetrazole" equilibrium is well known to the skilled person from Lakshman et al (2010) J. Org. Chem. 75, 2461-2473. Thus, references herein to azide extend equally to tetrazole as illustrated below when applied to the $R^3$ groups defined herein:

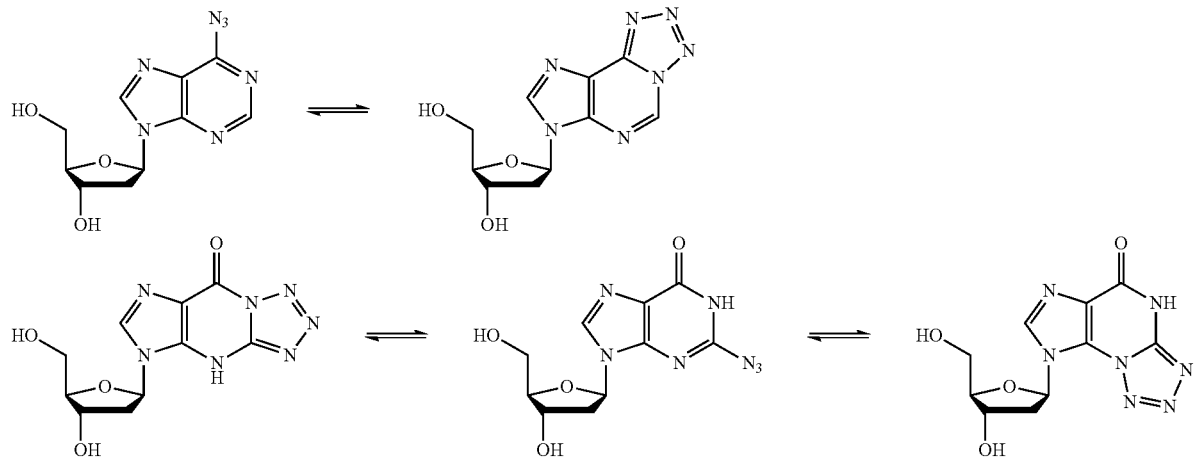

This embodiment has the advantage of reversibly masking the —$NH_2$ group. While blocked in the —$N_3$ state, the base (B) is impervious to deamination (e.g., deamination in the presence of sodium nitrite). The canonical cytosine, adenine, guanine can be respectively recovered from 4-azido cytosine, 6-azido adenine and 2-azido guanine by exposure to a reducing agent (e.g., TCEP). Thus, the —$N_3$ group serves as an effective protecting group against deamination, especially in the presence of sodium nitrite.

It will be appreciated that the compounds of the invention may be readily applied to methods of enzymatic nucleic acid synthesis which are well known to the person skilled in the art.

Non-limiting methods of nucleic acid synthesis may be found in WO 2016/128731, WO 2016/139477, WO 2017/009663, GB 1613185.6 and GB 1714827.1, the contents of each of which are herein incorporated by reference.

According to a further aspect of the invention, there is provided a compound of formula (I)$^a$:

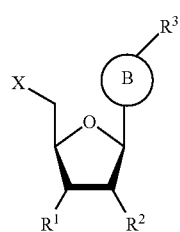

(I)$^a$ wherein:
$R^1$ represents a moiety capable of being unmasked to reveal a hydroxyl group, including —H, —OH, —$ONH_2$, —$ONC(CH_3)_2$, —$OCH_2N_3$, —$OCH_2CHCH_2$, —$OPO_3^{2-}$, —$OCH_2SSCH_2CH_3$, —$OCOCH_3$, —$OCH_2CH_2CN$, —O-methoxyethyl, —O-alkyl, or —O-alkoxy;

$R^2$ represents —H, —OH, —$ONH_2$, —$ONC(CH_3)_2$, —$OCH_2N_3$, —$OCH_2CHCH_2$, —$OPO_3^{2-}$, —$OCH_2SSCH_2CH_3$, —$OCOCH_3$, —$OCH_2CH_2CN$, —O-methoxyethyl, —O-alkyl, or —O-alkoxy or any other molecular moiety;

X represents one or more phosphate, phosphorothioate, boranophosphate or imidophosphate groups, or any combination thereof, wherein said group is capable of endowing competence for enzymatic addition;

$R^3$ represents an amine masking group, wherein said amino group would be involved in hydrogen bond base-pairing with a complementary base and deamination of said amino group could result in altered hydrogen bonding with a complementary base; and B represents a nitrogenous heterocycle.

According to a further aspect of the invention which may be mentioned, there is provided a compound of formula (I)$^a$:

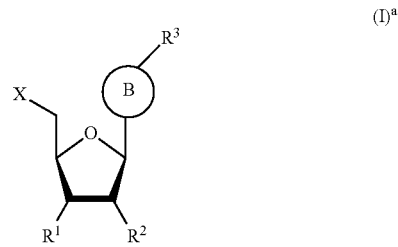

(I)$^a$ wherein:
$R^1$ and $R^2$ independently represent —H, —OH, —$ONH_2$, —$ONC(CH_3)_2$, —$OCH_2N_3$, —$OCH_2CHCH_2$, —O-methoxyethyl, —O-alkyl, —O-alkoxy, cyanoethyl, a thiol or a suitable hydroxy protecting group;

X represents one or more phosphate, phosphorothioate, boranophosphate or imidophosphate groups, or any combination thereof;

$R^3$ represents an amine masking group, wherein said amino group is involved in hydrogen bond base-pairing with a complementary base; and B represents a nitrogenous heterocycle.

In one embodiment, X represents a triphosphate group.

In one embodiment, $R^1$ and $R^2$ independently represent —H, —OH, —$ONH_2$, —$ONC(CH_3)_2$, —$OCH_2N_3$, —OCH₂CHCH₂, —OPO₃²⁻, —OCH₂SSCH₂CH₃, —OCOCH₃, —OCH₂CH₂CN, —O-methoxyethyl, —O-alkyl, or —O-alkoxy.

In an alternative embodiment, $R^1$ and $R^2$ independently represent —H, —OH, —ONH₂, —N₃, —OCH₂N₃, —ONC(CH₃)₂, —OCH₂CHCH₂, —O-methoxyethyl, —O-alkyl, —O-alkoxy, cyanoethyl, a thiol or a suitable hydroxy protecting group.

Examples of suitable amine masking groups for $R^3$ include azide (—N₃), benzoylamine (N-benzoyl or —NHCOPh), N-methyl, (—NHMe), isobutyrylamine, dimethylformamidylamine, 9-fluorenylmethyl carbamate, t-butyl carbamate, benzyl carbamate, acetamide (N-acetyl or —NHCOMe), trifluoroacetamide, pthlamide, benzylamine (N-benzyl or —NH—CH₂-phenyl), triphenylmethylamine, benxylideneamine, tosylamide, isothiocyanate, N-allyl (such as N-dimethylallyl (—NHCH₂—CH=CH₂)) and N-anisoyl (—NHCOPh-OMe), such as azide (—N₃), N-acetyl (—NHCOMe), N-benzyl (—NH—CH₂-phenyl), N-anisoyl (—NHCOPh-OMe), N-methyl, (—NHMe), N-benzoyl (—NHCOPh), N-dimethylallyl (—NHCH₂—CH=CH₂).

In one embodiment, B represents a nitrogenous heterocycle selected from a purine or pyrimidine. In a further embodiment, B and R3 can be combined into the following molecular structures, where the nitrogenous heterocycle is connected to the (deoxyribose) 1' position of the compound of formula (I):

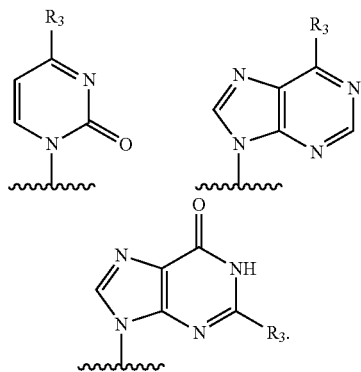

In one embodiment, $R^3$ represents an azide (—N₃) group and B is selected from:

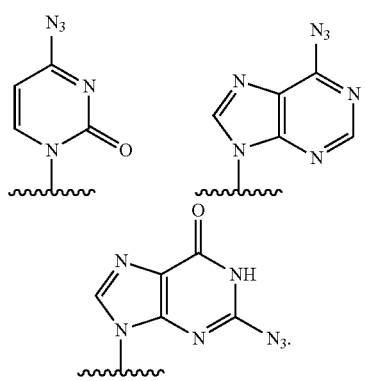

One particular compound of formula (I)ᵃ which may be mentioned (1) is one wherein $R^1$ represents —ONH₂, $R^2$ represents H, X represents a triphosphate group, B represents:

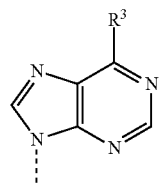

and $R^3$ represents N₃, thus a compound of formula (1):

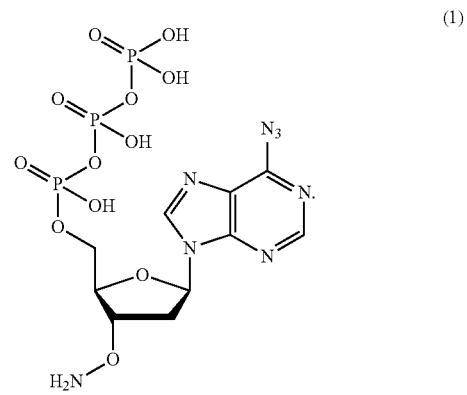

(1)

The compound of formula (1) may be prepared in accordance with the following synthetic scheme:

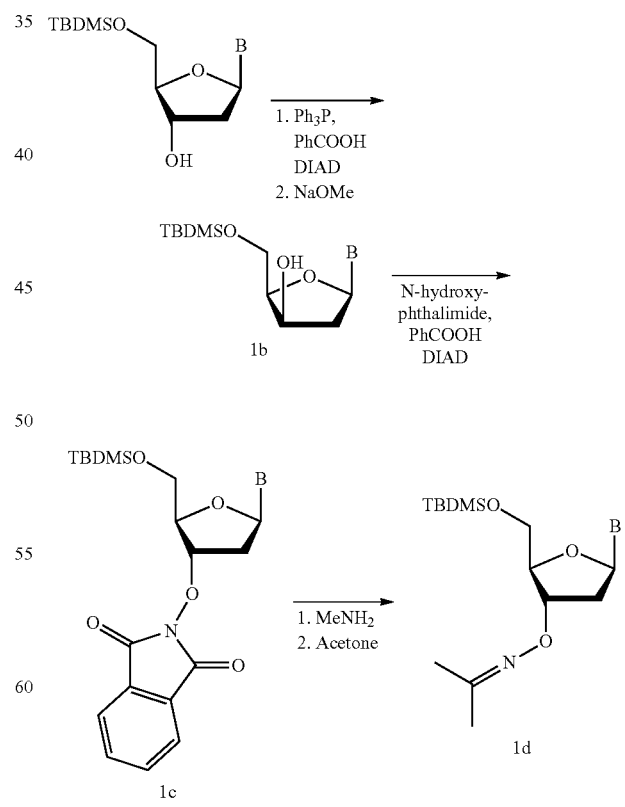

1a, B = inosine

-continued

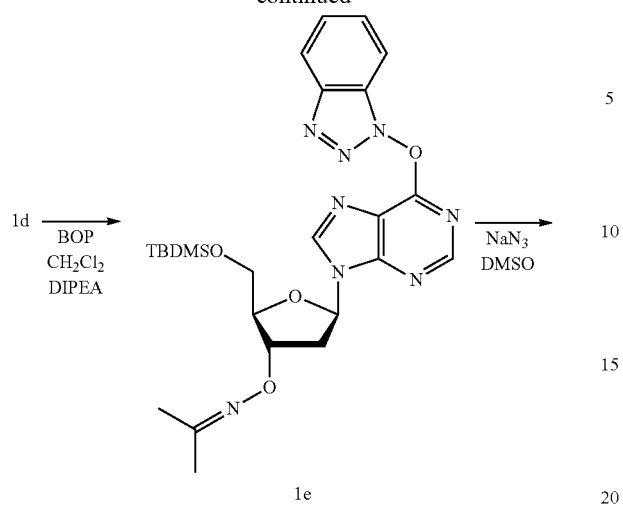

1e

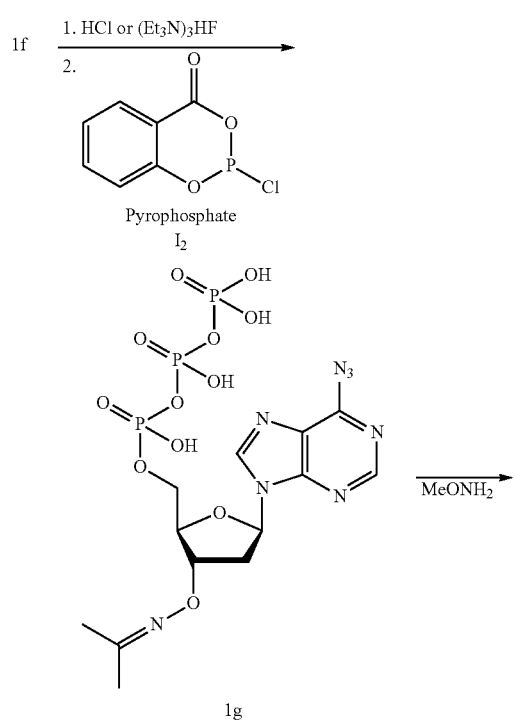

1f

1. HCl or (Et₃N)₃HF
2.

Pyrophosphate I₂

MeONH₂

1g

-continued

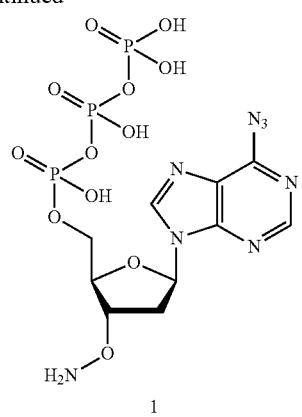

1

One further particular compound of formula (I)ᵃ which may be mentioned (2) is one wherein $R^1$ represents —ONH₂, $R^2$ represents H, X represents a triphosphate group, B represents:

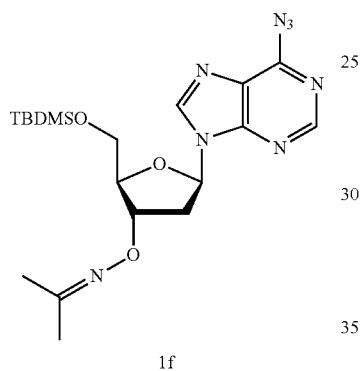

and $R^3$ represents N₃, thus a compound of formula (2):

(2)

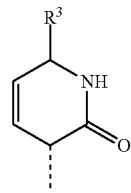

The compound of formula (2) may be prepared in accordance with the following synthetic scheme:

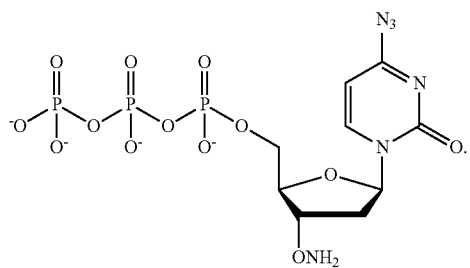

1. Ph₃P, PhCOOH DIAD
2. NaOMe

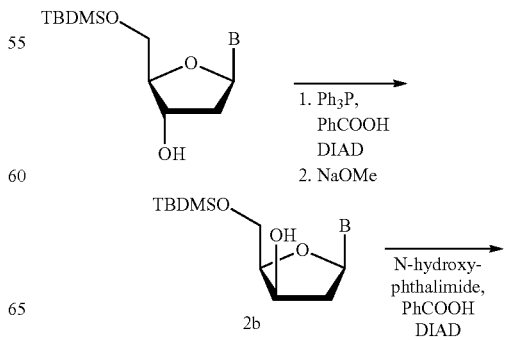

2b

N-hydroxy-phthalimide, PhCOOH DIAD

23
-continued

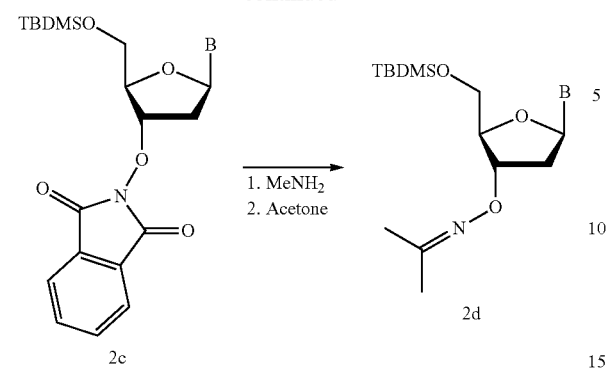

2a, B = deoxythymidine

2d $\xrightarrow{\text{p-ClPhOPOCl}_2}{\text{Pyridine}}$

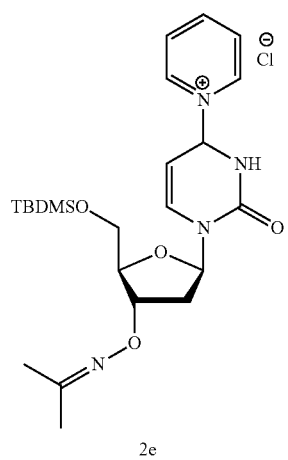

2e

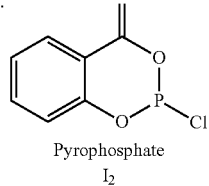

2f $\xrightarrow[\text{2.}]{\text{1. HCl or (Et}_3\text{N)}_3\text{HF}}$

Pyrophosphate
I$_2$

24
-continued

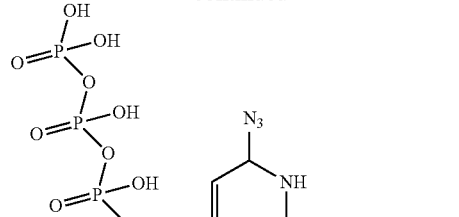

2g $\xrightarrow{\text{MeONH}_2}$

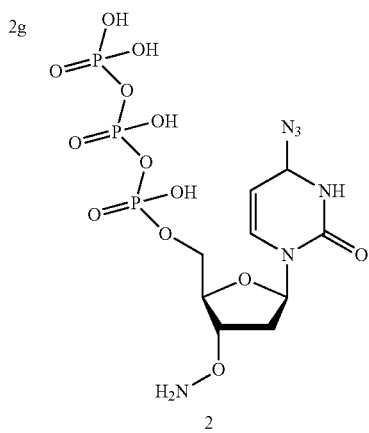

2

One further particular compound of formula (I)$^a$ which may be mentioned (3) is one wherein R$^1$ represents —ONH$_2$, R$^2$ represents H, X represents a triphosphate group, B represents:

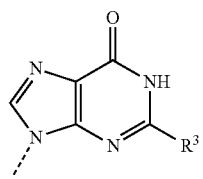

and R$^3$ represents N$_3$, thus a compound of formula (3):

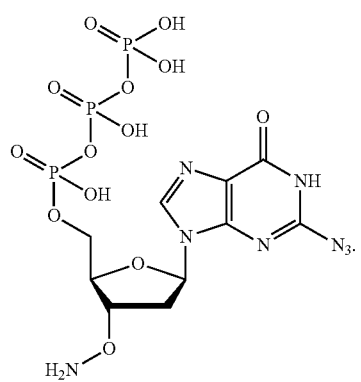

(3)

The compound of formula (3) may be prepared in accordance with the following synthetic scheme:
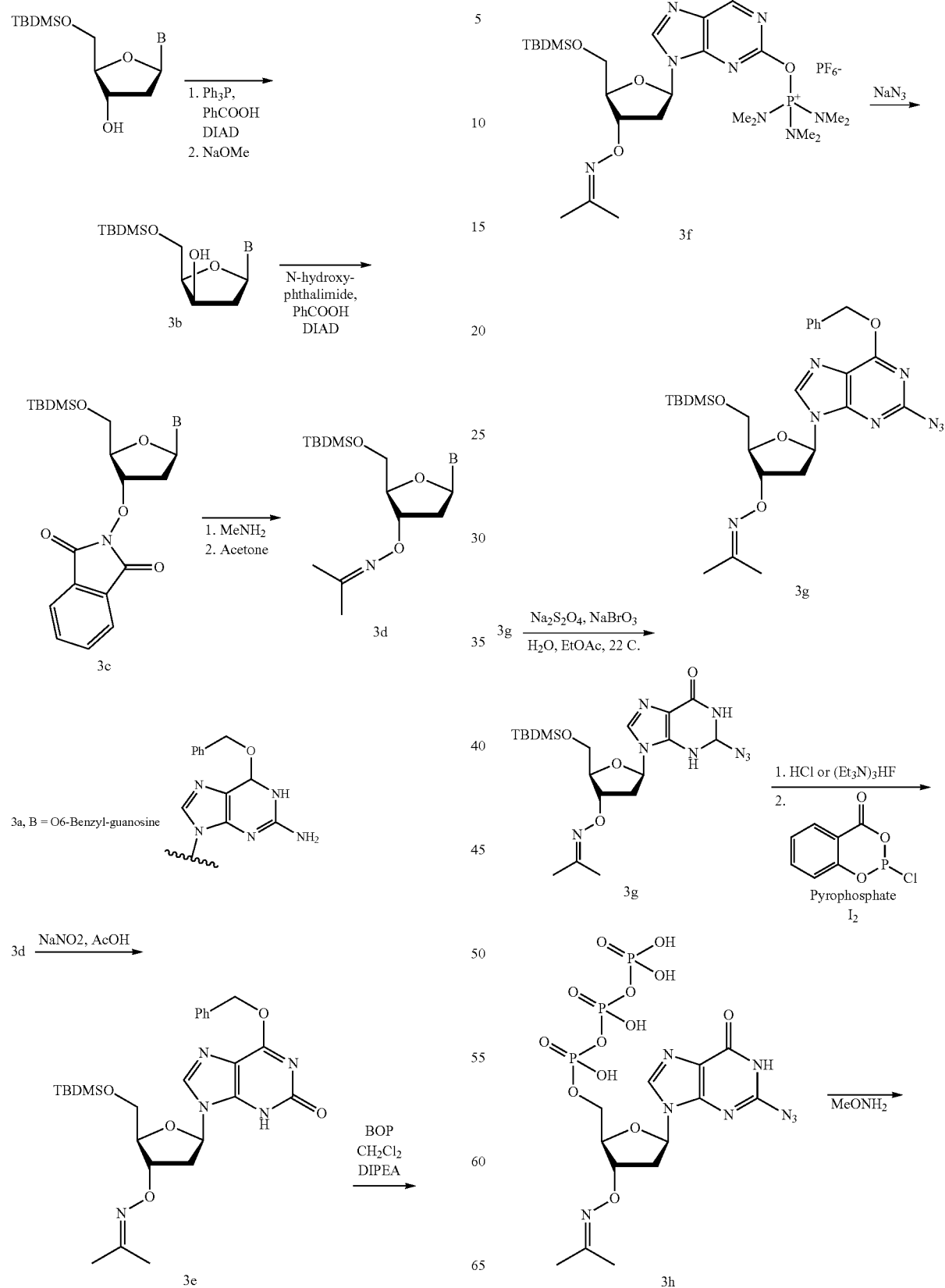

-continued

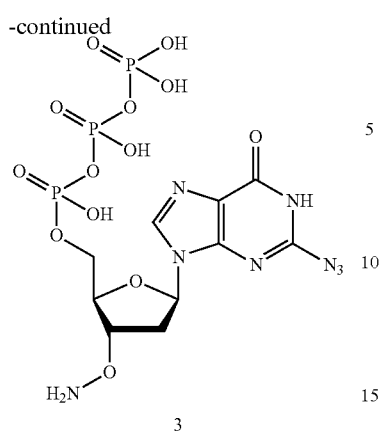

3

In another embodiment, R³ represents an acetyl (—Ac) group and B is selected from:

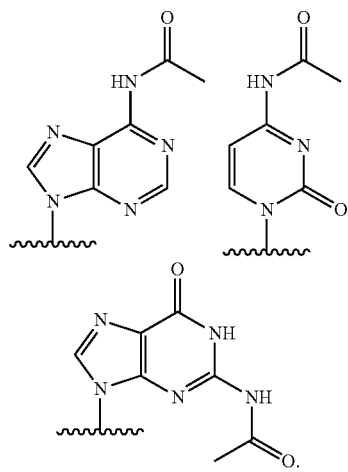

In another embodiment, R³ represents an anisoyl group and B is selected from:

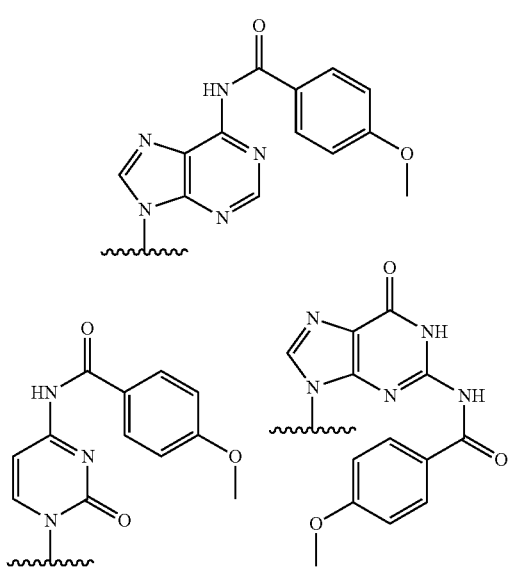

In another embodiment, R³ represents a benzyl group and B is selected from:

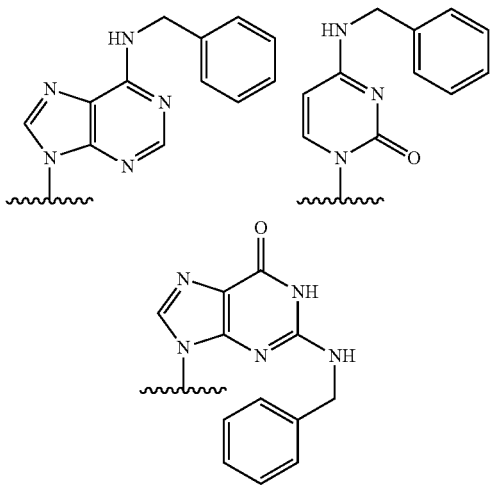

In another embodiment, R³ represents a benzyl group and B is selected from:

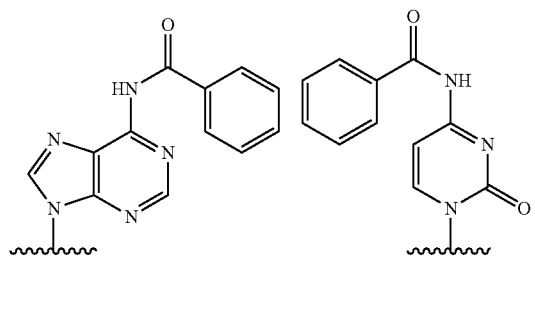

In another embodiment R³ represents a methyl group and R is selected from:

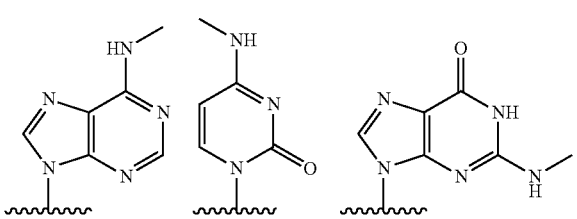

In another embodiment, R³ represents an allyl group and B is selected from:

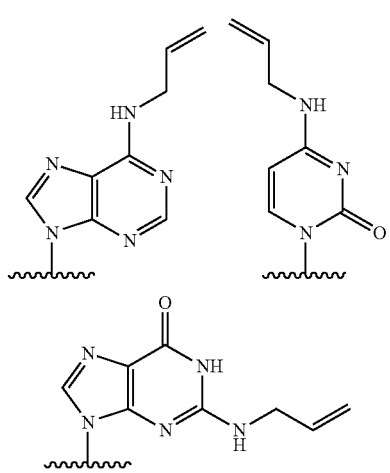
Particular compounds of formula (I)$^a$ which may be mentioned (4-27) are those wherein $R^1$ represents —$ONH_2$, $R^2$ represents H, X represents a triphosphate group and B represents the bases described above, resulting in compounds:
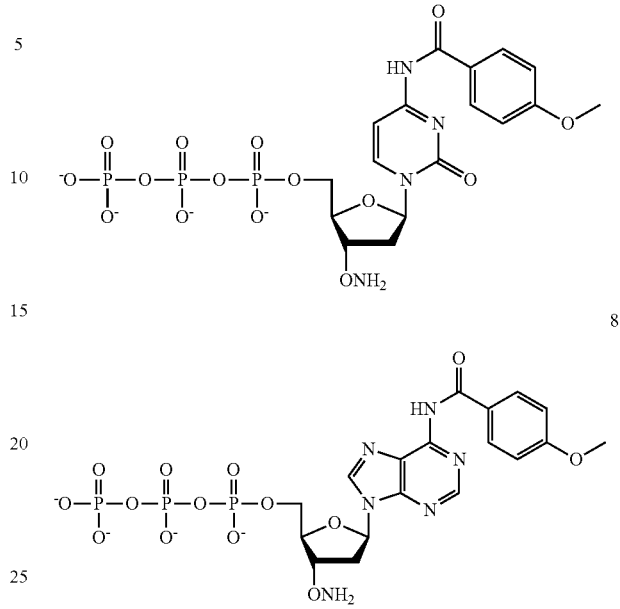
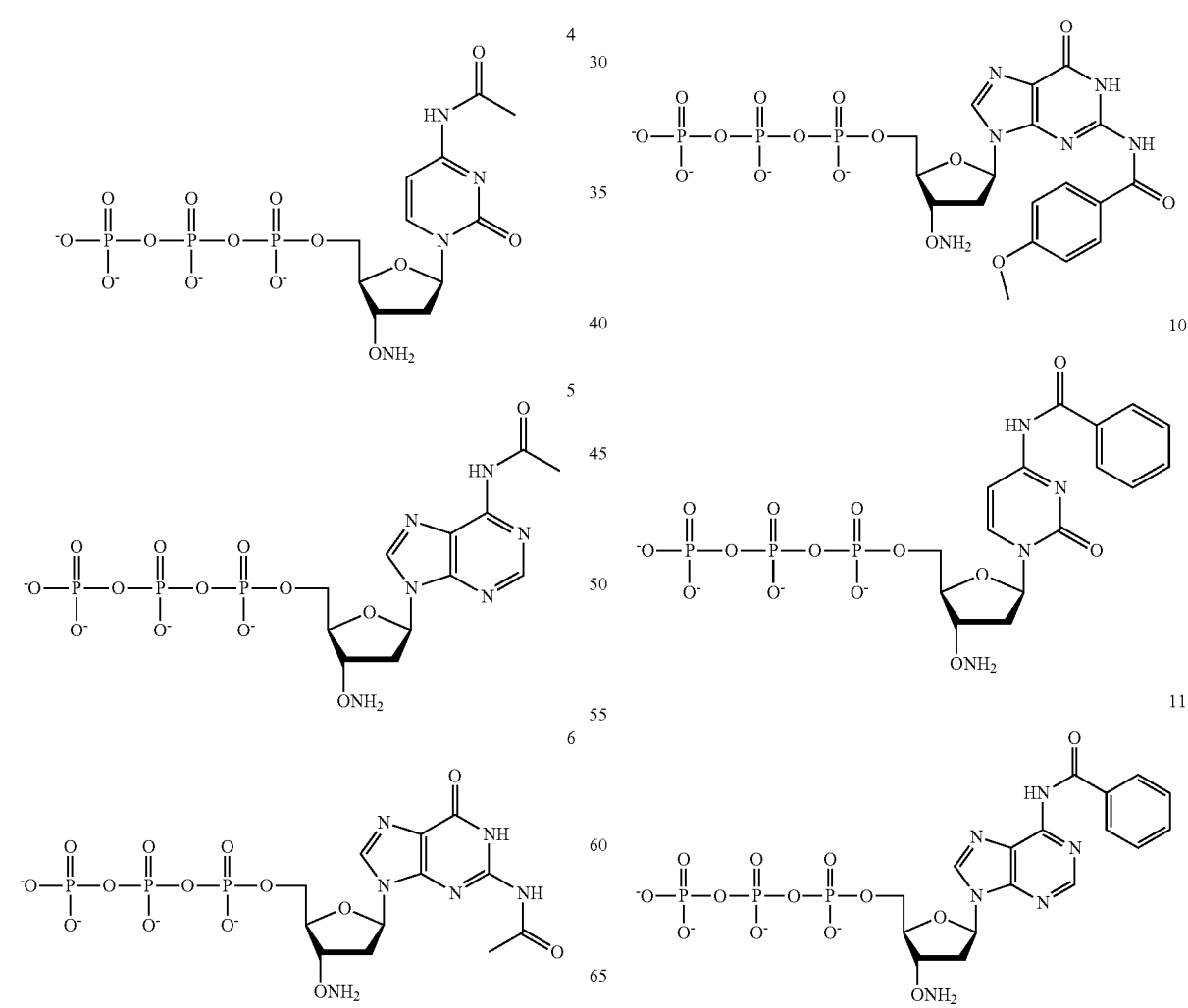

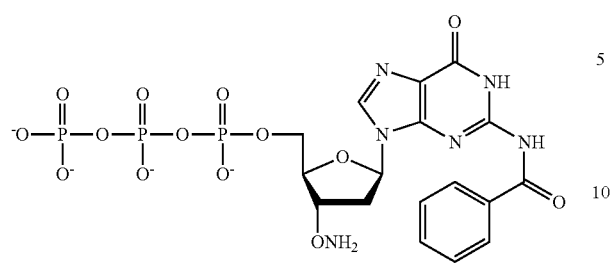
12
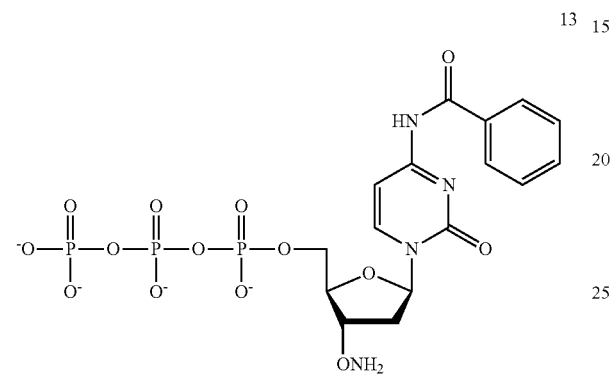
13
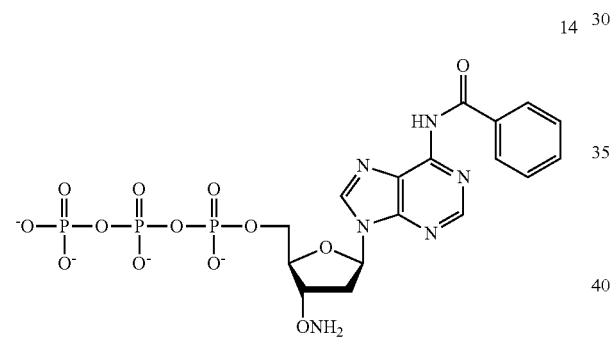
14
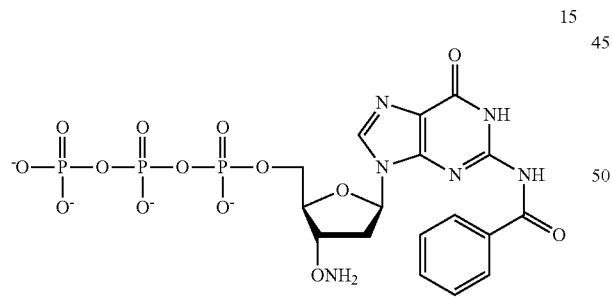
15
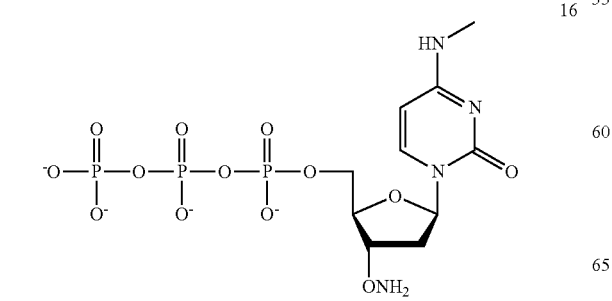
16
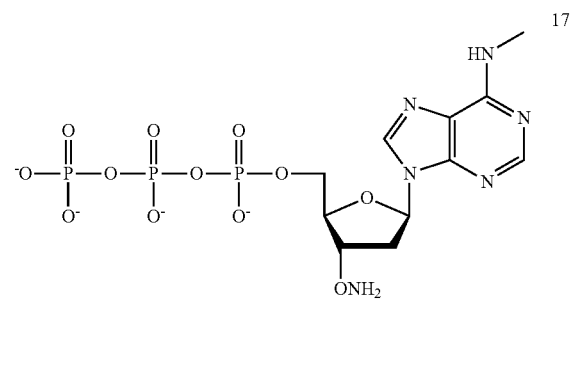
17
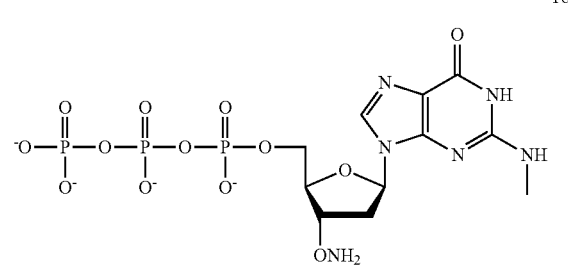
18
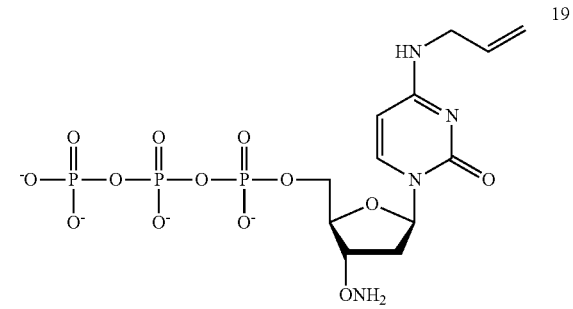
19
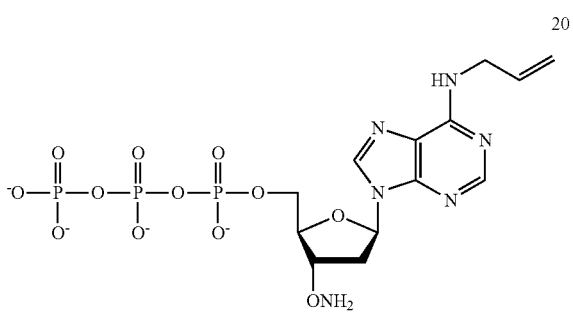
20
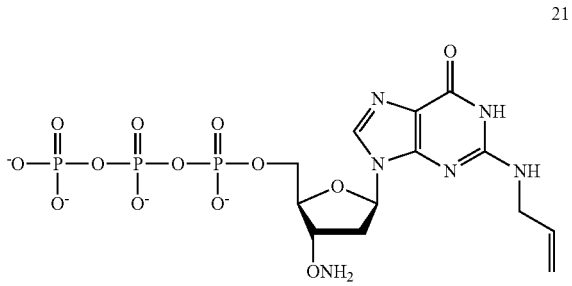
21

22

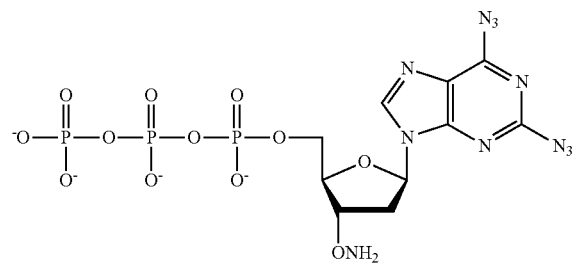

23

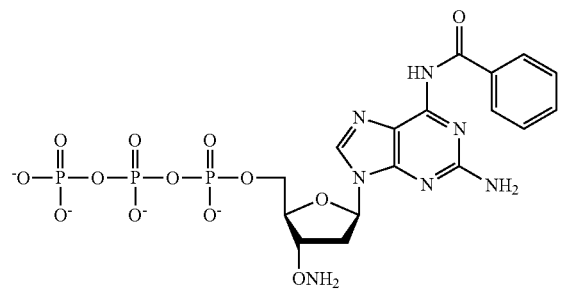

24

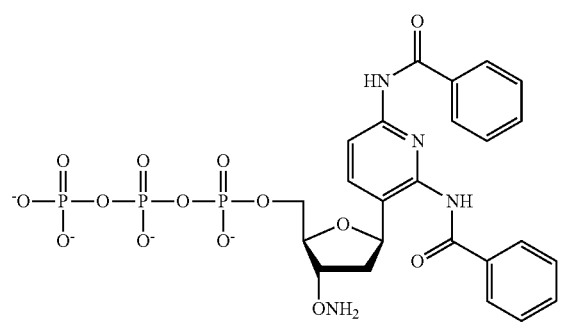

25

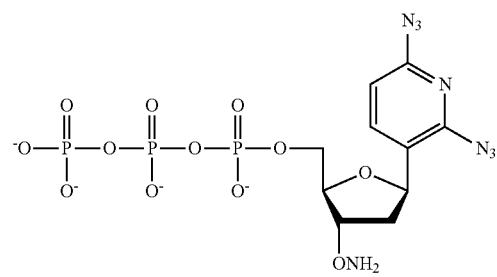

26

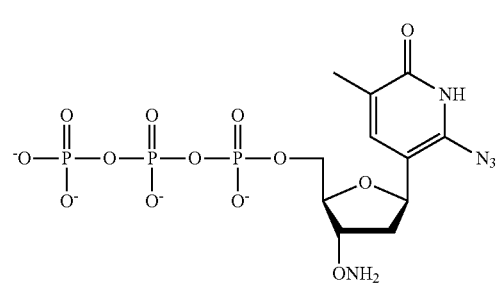

27

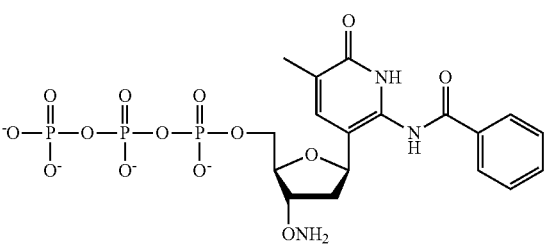

According to a further aspect of the invention, there is provided a process of preparing a compound of formula (V):

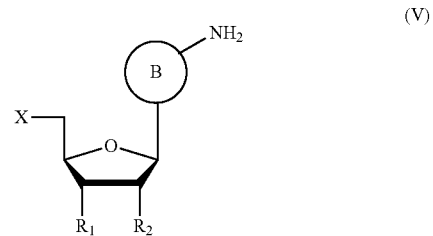

(V)

wherein X, $R^1$, $R^2$ and B are as defined herein, which comprises reacting a compound of formula (I):

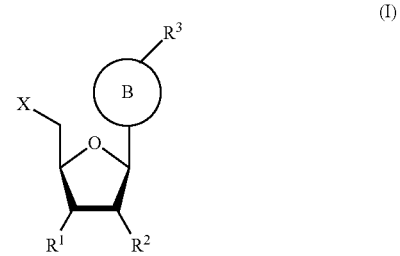

(I)

wherein X, $R^1$, $R^2$, $R^3$ and B are as defined herein, with a chemical, with electromagnetic radiation, with heat and/or with an electric current.

According to a further aspect of the invention, there is provided a process of preparing a compound of formula (II), (III) or (IV):

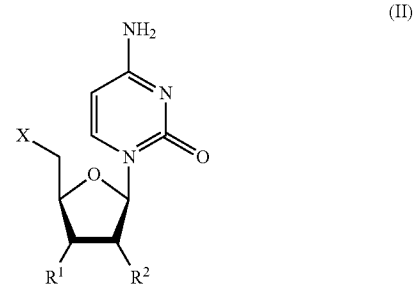

(II)

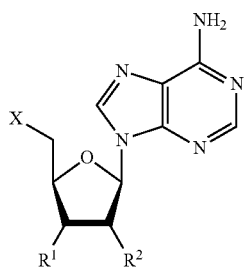
(III)

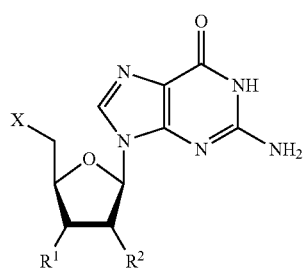
(IV)

wherein X, $R^1$ and $R^2$ are as defined herein, which comprises reacting a compound of formula $(II)^a$, $(III)^a$ or $(IV)^a$, respectively:

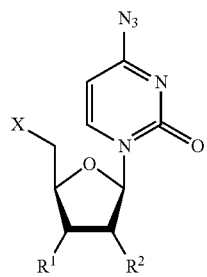
$(II)^a$

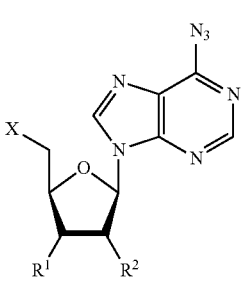
$(III)^a$

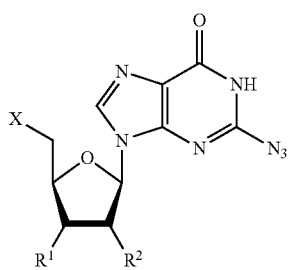
$(IV)^a$ wherein X, $R^1$ and $R^2$ are as defined herein, with a chemical, with electromagnetic radiation and/or with an electric current.

According to a further aspect of the invention, there is provided a process of preparing a compound of formula (II), (III) or (IV) as defined herein, which comprises reacting a compound of formula (VI):

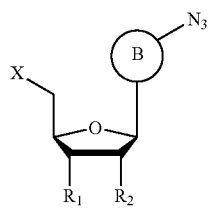
(VI)

wherein X, $R^1$, $R^2$ and B are as defined herein, with a reducing agent.

In one embodiment, the reducing agent is selected from beta-mercaptoethanol, dithiothreitol or a phosphine-based reducing agent such as tris(hydroxymethyl)phosphine (THP). tris(hydroxypropyl)phosphine (THPP) and tris(2-carboxylethyl)phosphine (TCEP).

According to a further aspect of the invention, there is provided a compound of formula (VII):

(VII)

wherein $R^2$ represents —H, —OH, —ONH$_2$, —ONC(CH$_3$)$_2$, —OCH$_2$N$_3$, —OCH$_2$CHCH$_2$, —OPO$_3^{2-}$, —OCH$_2$SSCH$_2$CH$_3$, —OCOCH$_3$, —OCH$_2$CH$_2$CN, —O-methoxyethyl, —O-alkyl, or —O-alkoxy or a suitable hydroxy protecting group;

X represents one or more phosphate, phosphorothioate, boranophosphate or imidophosphate groups, or any combination thereof; and $R^4$ represents $C_{2-6}$ alkyl, —F, —Cl, —Br, —I, alkoxy, biotin, alkylamine or azide.

According to a further aspect of the invention, there is provided the use of a compound of formula (VII) in a method of enzymatic nucleic acid synthesis.

In one embodiment, the method of enzymatic nucleic acid synthesis is selected from a method of reversibly terminated enzymatic nucleic acid synthesis and a method of templated and non-templated de novo enzymatic nucleic acid synthesis.

The following studies illustrate the invention:

Example 1: Enzymatic DNA Synthesis Using Azide-Masked Nitrogenous Heterocycles

In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with an azido group to prevent oxidative deamination (FIG. 1-4). For example, one or a combination of 2'-deoxy-3'-O-aminoxy-N4-azidocytidine 5'-triphosphate, 2'-deoxy-3'-O-aminoxy-N6-azidoadenine 5'-triphosphate, 2'-deoxy-3'-O-aminoxy-N2-azidoguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-azidocytosine, N6-azidoadenine, N2-azidoguanine) is thus synthesized. All amine-masked nitrogenous heterocycles are unmasked to reveal an amino group through exposure to a reducing agent (e.g., TCEP). The DNA polymer is now composed of nitrogenous heterocycles with unmasked amino groups (e.g., N4-azidocytosine is unmasked to cytosine, N6-azidoadenine is unmasked to adenine and N2-azidoguanine is unmasked to guanine). The DNA polymer can now be used for downstream molecular biology applications.

Example 2: Enzymatic DNA Synthesis Using N-Acetyl-Masked Nitrogenous Heterocycles In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with an acetyl group to protect from oxidative deamination (FIGS. 6 and 7). For example, one or a combination of 2'-deoxy-3'-O-aminoxy-N4-acetylcytidine 5'-triphosphate, 2'-deoxy-3'-O-aminoxy-N6-acetyladenine 5'-triphosphate, 2'-deoxy-3'-O-aminoxy-N2-acetylguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-acetylcytosine, N6-acetyladenine, N2-acetylguanine) is thus synthesized. All amine-masked nitrogenous heterocycles are deacetylated and thus unmasked to reveal an amino group through exposure to a base (e.g., potassium carbonate) as shown in FIGS. 6 and 7. The DNA polymer is now composed of nitrogenous heterocycles with unmasked amino groups (e.g., N4-acetlycytosine is unmasked to cytosine, N6-acetyladenine is unmasked to adenine and N2-acetylguanine is unmasked to guanine). The DNA polymer can now be used for downstream molecular biology applications.

Example 3: Enzymatic DNA Synthesis Using N-Benzoyl- and N-Anisoyl-Masked Nitrogenous Heterocycles In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with a benzoyl group to protect from oxidative deamination (FIGS. 9 and 12). For example, one or a combination of 2'-deoxy-3'-O-aminoxy-N4-benzoylcytidine 5'-triphosphate, 2'-deoxy-3'-O-aminoxy-N6-benzoyladenine 5'-triphosphate, 2'-deoxy-3'-O-aminoxy-N2-benzoylguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-benzoylcytosine, N6-benzoyladenine, N2-benzoylguanine) is thus synthesized. All amine-masked nitrogenous heterocycles are debenzoylated and thus unmasked to reveal an amino group through exposure to a base (e.g., methylamine) as shown in FIGS. 9 and 12. The DNA polymer is now composed of nitrogenous heterocycles with unmasked amino groups (e.g., N4-acetlycytosine is unmasked to cytosine, N6-benzoyladenine is unmasked to adenine and N2-benzoylguanine is unmasked to guanine). The DNA polymer can now be used for downstream molecular biology applications.

Example 4: Enzymatic DNA Synthesis Using N-Benzyl-Masked Nitrogenous Heterocycles In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with a benzyl group to protect from oxidative deamination (FIG. 8). For example, one or a combination of 2'-deoxy-3'-O-aminoxy-N4-benzylcytidine 5'-triphosphate, 2'-deoxy-3'-O-aminoxy-N6-benzyladenine 5'-triphosphate, 2'-deoxy-3'-O-aminoxy-N2-benzylguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-benzylcytosine, N6-benzyladenine, N2-benzylguanine) is thus synthesized. All amine-masked nitrogenous heterocycles are debenzylated and thus unmasked to reveal an amino group through hydrogenolysis (e.g., Pd-C) or tert-butoxide and $O_2$ in DMSO. The DNA polymer is now composed of nitrogenous heterocycles with unmasked amino groups (e.g., N4-acetlycytosine is unmasked to cytosine, N6-benzyladenine is unmasked to adenine and N2-benzylguanine is unmasked to guanine). The DNA polymer can now be used for downstream molecular biology applications.

Example 5: Enzymatic DNA Synthesis Using N-Methyl-Masked Nitrogenous Heterocycles In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with a methyl group. For example, one or a combination of 2'-deoxy-3'-O-aminoxy-N4-methylcytidine 5'-triphosphate, 2'-deoxy-3'-O-aminoxy-N6-methyladenine 5'-triphosphate, 2'-deoxy-3'-O-aminoxy-N2-methylguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-methylcytosine, N6-methyladenine, N2-methylguanine) is thus synthesized. All amine-masked nitrogenous heterocycles are demethylated and thus unmasked to reveal an amino group through exposure to demethylases. For example, the amine-masked DNA polymer can be exposed to a cocktail of known demethylases or one single demethylase such as the DNA repair enzyme AlkB. The DNA polymer is now composed of nitrogenous heterocycles with unmasked amino groups (e.g., N4-acetlycytosine is unmasked to cytosine, N6-methyladenine is unmasked to adenine and N2-methylguanine is unmasked to guanine). The DNA polymer can now be used for downstream molecular biology applications.

Example 6: Enzymatic DNA Synthesis Using N-Allyl-Masked Nitrogenous Heterocycles In the following method of DNA synthesis, engineered terminal deoxynucleotidyl transferase is used to add 3'-O-aminoxy reversibly terminated 2'-deoxynucleoside 5'-triphosphates to the 3'-end of DNA strands. This addition process is repeated until a desired sequence is synthesized. The 3'-O-aminoxy moiety must be deaminated (e.g., with acidic sodium nitrite) after each addition cycle to effect reversible termination. The process of deamination after each addition cycle also results in the mutagenic deamination of nitrogenous heterocycles containing amines (e.g., adenine, cytosine and guanine).

Thus, in this example, amino moieties on the nitrogenous heterocycles are masked with a allyl group to protect from oxidative deamination (FIG. 10). For example, one or a combination of 2'-deoxy-3'-O-aminoxy-N4-allylcytidine 5'-triphosphate, 2'-deoxy-3'-O-aminoxy-N6-allyladenine 5'-triphosphate, 2'-deoxy-3'-O-aminoxy-N2-allylguanosine 5'-triphosphate and 2'-deoxy-3'-O-aminoxy-5-ethyluridine 5'-triphosphate are used as nucleotide building blocks during each addition cycle in the presence of engineered TdT and required buffer components.

A DNA polymer with amine-masked nitrogenous heterocycles (e.g., N4-allylcytosine, N6-allyladenine, N2-allylguanine) is thus synthesized. All amine-masked nitrogenous heterocycles are deallylated and thus unmasked to reveal an amino group through exposure to tetrakis(triphenylphosphine) palladium. The DNA polymer is now composed of nitrogenous heterocycles with unmasked amino groups (e.g., N4-acetlycytosine is unmasked to cytosine, N6-allyladenine is unmasked to adenine and N2-allylguanine is unmasked to guanine). The DNA polymer can now be used for downstream molecular biology applications.

The invention claimed is:

1. A method of non-templated enzymatic nucleic acid synthesis comprising:

(i) providing a compound of formula (I):

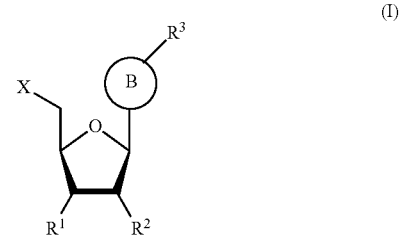

wherein:

$R^1$ represents —$ONH_2$, —$ONC(CH_3)_2$, —$OCH_2N_3$, —$OCH_2CHCH_2$, —$OPO_3^{2-}$, —$OCH_2SSCH_2CH_3$, —$OCOCH_2$, —$OCH_2CH_2CN$, —O-methoxyethyl;

$R^2$ represents —H,

X represents a triphosphate group;

$R^3$ represents an amine masking group selected from an azide, benzoylamine, isobutyrylamine, dimethylformamidylamine, 9-fluorenylmethyl carbamate, t-butyl carbamate, benzyl carbamate, acetamide, trifluoroacetamide, pthlamide, benzylamine, triphenylmethylamine, benxylideneamine, tosylamide, isothiocyanate, N-allyl or N-anisoyl; and B represents a nitrogenous heterocycle selected from a purine or pyrimidine;

(ii) incorporating the compound of formula (I) into a nucleic acid molecule;

(iii) repeating steps (i) and (ii) until a desired nucleic acid sequence having the amine masking group is synthesized; and (iv) unmasking the $R^3$ amine masking group to reveal an amino(—$NH_2$) group.

2. The method of claim 1, wherein the compound of formula (I) is selected from:

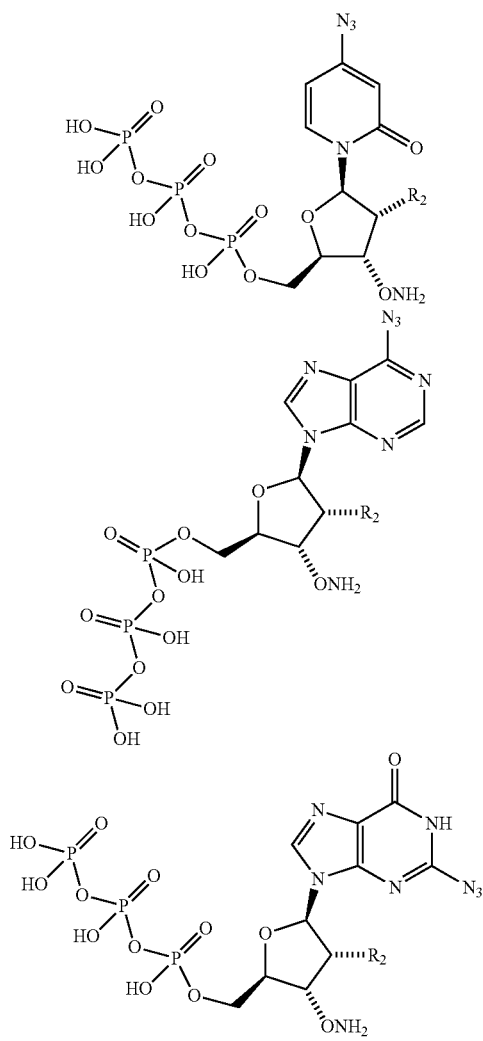

where R₂ represents —H.

3. The method of claim 1, wherein R¹ represents —ONH₂, —ONC(CH₃)₂, or —OCH₂N₃.

4. A compound of formula (I)$^a$:

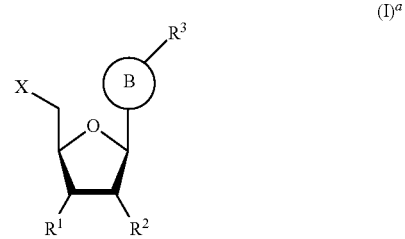

wherein:

R¹ represents —ONH₂, —ONC(CH₃)₂ or —OCH₂N₃;

R² represents —H;

X represents a triphosphate group;

R³ represents azide, benzoyl amine, isobutyrylamine, dimethylformamidylamine, 9-fluorenylmethyl carbamate, t-butyl carbamate, benzyl carbamate, acetamide, trifluoroacetamide, pthlamide, benzylamine, triphenylmethylamine, benxylideneamine, tosylamide, isothiocyanate, N-allyl or N-anisoyl, and B represents a nitrogenous heterocycle selected from a purine or pyrimidine.

5. The method of claim 1, wherein the unmasking comprises unmasking with a reducing agent.

6. The method of claim 5, wherein the reducing agent is selected from beta-mercaptoethanol, dithiothreitol or a phosphine-based reducing agent.

* * * * *